(12) United States Patent
Holley et al.

(10) Patent No.: US 11,160,941 B2
(45) Date of Patent: Nov. 2, 2021

(54) METHOD AND APPARATUS FOR ORAL FLOW THERAPY

(71) Applicant: ResMed Pty Ltd, Bella Vista (AU)

(72) Inventors: Liam Holley, Sydney (AU); Glenn Richards, Auckland (NZ); Peter Wlodarczyk, Ashfield (AU); Ning Wang, Glenwood (AU)

(73) Assignee: ResMed Pty Ltd

( * ) Notice: Subject to any disclaimer, the term of this patent is extended or adjusted under 35 U.S.C. 154(b) by 1478 days.

(21) Appl. No.: 14/395,925

(22) PCT Filed: Apr. 30, 2013

(86) PCT No.: PCT/AU2013/000445
§ 371 (c)(1),
(2) Date: Oct. 21, 2014

(87) PCT Pub. No.: WO2013/163685
PCT Pub. Date: Nov. 7, 2013

(65) Prior Publication Data
US 2015/0128941 A1    May 14, 2015

(30) Foreign Application Priority Data
Apr. 30, 2012   (AU) .............................. 2012901699

(51) Int. Cl.
*A61M 16/00*  (2006.01)
*A61M 16/16*  (2006.01)
(Continued)

(52) U.S. Cl.
CPC .... *A61M 16/0069* (2014.02); *A61M 16/0003* (2014.02); *A61M 16/024* (2017.08);
(Continued)

(58) Field of Classification Search
CPC .......... A61M 16/0069; A61M 16/0003; A61M 16/049; A61M 16/0616; A61M 16/0833;
(Continued)

(56) References Cited

U.S. PATENT DOCUMENTS

| 4,944,310 A | 7/1990 | Sullivan |
| 6,349,724 B1 * | 2/2002 | Burton .............. A61M 16/0057 128/204.18 |

(Continued)

FOREIGN PATENT DOCUMENTS

| DE | 4445652 A1 | 6/1996 |
| EP | 0818213 A2 | 1/1998 |

(Continued)

OTHER PUBLICATIONS

International Preliminary Report on Patentability for Application No. PCT/AU2013/000445 dated Aug. 26, 2014.
(Continued)

*Primary Examiner* — Elliot S Ruddie
(74) *Attorney, Agent, or Firm* — Botos Churchill IP Law LLP

(57) ABSTRACT

A therapy system configured to wash out or flush out the oral and/or nasal cavity to reduce the effective dead space and reduce the work of breathing. The system may displace the expired air in the oral and/or nasal cavity with atmospheric air, or air with altered concentrations, for example, increased humidity, or oxygen levels. A sealed oral interface is provided to the mouth of a patient to supply a volume of pressurized gas. A control system to synchronize the supply of pressurized gas with the patients respiratory cycle. The supply of respiratory gas may be provided during only a portion of the respiratory cycle.

14 Claims, 27 Drawing Sheets

(51) Int. Cl.

| | | |
|---|---|---|
| *A61M 16/06* | (2006.01) | |
| *A61M 16/12* | (2006.01) | |
| *A61M 16/10* | (2006.01) | |
| *A61M 16/04* | (2006.01) | |
| *A61M 16/08* | (2006.01) | |
| *A61M 16/20* | (2006.01) | |
| *A61M 16/22* | (2006.01) | |

(52) U.S. Cl.
CPC ...... *A61M 16/049* (2014.02); *A61M 16/0488* (2013.01); *A61M 16/0616* (2014.02); *A61M 16/0666* (2013.01); *A61M 16/0683* (2013.01); *A61M 16/0833* (2014.02); *A61M 16/107* (2014.02); *A61M 16/1045* (2013.01); *A61M 16/1055* (2013.01); *A61M 16/1065* (2014.02); *A61M 16/12* (2013.01); *A61M 16/125* (2014.02); *A61M 16/16* (2013.01); *A61M 16/20* (2013.01); *A61M 16/22* (2013.01); *A61M 2016/003* (2013.01); *A61M 2016/0027* (2013.01); *A61M 2016/0039* (2013.01); *A61M 2202/0014* (2013.01); *A61M 2202/0208* (2013.01); *A61M 2202/0225* (2013.01); *A61M 2205/3334* (2013.01); *A61M 2205/3365* (2013.01); *A61M 2205/36* (2013.01); *A61M 2205/52* (2013.01); *A61M 2205/82* (2013.01); *A61M 2210/0625* (2013.01); *A61M 2230/00* (2013.01)

(58) Field of Classification Search
CPC ............ A61M 16/1065; A61M 16/107; A61M 16/125; A61M 16/0051; A61M 16/0488; A61M 16/0666; A61M 16/0683; A61M 16/1045; A61M 16/1055; A61M 16/12; A61M 16/16; A61M 16/20; A61M 2016/049; A61M 2016/0493; A61M 2016/0495; A61M 16/22; A61M 2016/0027; A61M 2016/003; A61M 2016/0039; A61M 2202/0014; A61M 2202/0208; A61M 2202/0225; A61M 2205/3334; A61M 2205/3365; A61M 2205/36; A61M 2205/52; A61M 2205/82; A61M 2210/0625; A61M 2230/00; A61F 5/56; A61F 5/566
USPC .................. 128/204.21, 859, 861
See application file for complete search history.

(56) References Cited

U.S. PATENT DOCUMENTS

| | | | |
|---|---|---|---|
| 6,532,959 B1 | 3/2003 | Berthon-Jones | |
| 2004/0112381 A1 | 6/2004 | Ujhazy et al. | |
| 2004/0216740 A1 | 11/2004 | Remmers et al. | |
| 2004/0237965 A1 | 12/2004 | Bibi et al. | |
| 2005/0150504 A1 | 7/2005 | Heeke et al. | |
| 2006/0282010 A1* | 12/2006 | Martin ............... | A61B 5/4205 600/560 |
| 2007/0161918 A1* | 7/2007 | Ganshorn ............ | A61B 5/085 600/533 |
| 2007/0175473 A1 | 8/2007 | Lewis et al. | |
| 2008/0178880 A1 | 7/2008 | Christopher et al. | |
| 2009/0044805 A1* | 2/2009 | Somaiya ......... | A61M 16/0051 128/204.22 |
| 2009/0101147 A1 | 4/2009 | Landis et al. | |
| 2009/0107494 A1 | 4/2009 | Freitag et al. | |
| 2009/0120447 A1* | 5/2009 | Vaska ..................... | A61F 5/566 128/848 |
| 2009/0127947 A1 | 5/2009 | Kim et al. | |
| 2009/0133696 A1 | 5/2009 | Remmers et al. | |
| 2010/0071693 A1* | 3/2010 | Allum .................. | A61M 16/04 128/203.27 |
| 2010/0158854 A1 | 6/2010 | Puisais | |
| 2010/0319697 A1 | 12/2010 | Farrugia et al. | |
| 2011/0027746 A1 | 2/2011 | McDonough et al. | |
| 2011/0270166 A1 | 11/2011 | Martin et al. | |
| 2013/0284166 A1* | 10/2013 | Colla .................. | A61M 16/00 128/202.22 |

FOREIGN PATENT DOCUMENTS

| | | |
|---|---|---|
| EP | 1126893 A1 | 8/2001 |
| WO | 1998043539 A1 | 10/1998 |
| WO | 0027457 A1 | 5/2000 |
| WO | 2009003137 A1 | 12/2008 |
| WO | 2011051896 A2 | 5/2011 |
| WO | 2012045051 A1 | 4/2012 |

OTHER PUBLICATIONS

International Search Report and Written Opinion for Application No. PCT/AU2013/000445 dated Jul. 22, 2013.
International Written Opinion for Application No. PCT/AU2013/000445 dated Apr. 2, 2014.
Partial Supplementary European Search Report for Application No. 13784742.2 dated Oct. 28, 2015.
EP Search Report dated Jul. 8, 2020 for EP Application No. 19211280.0.

* cited by examiner

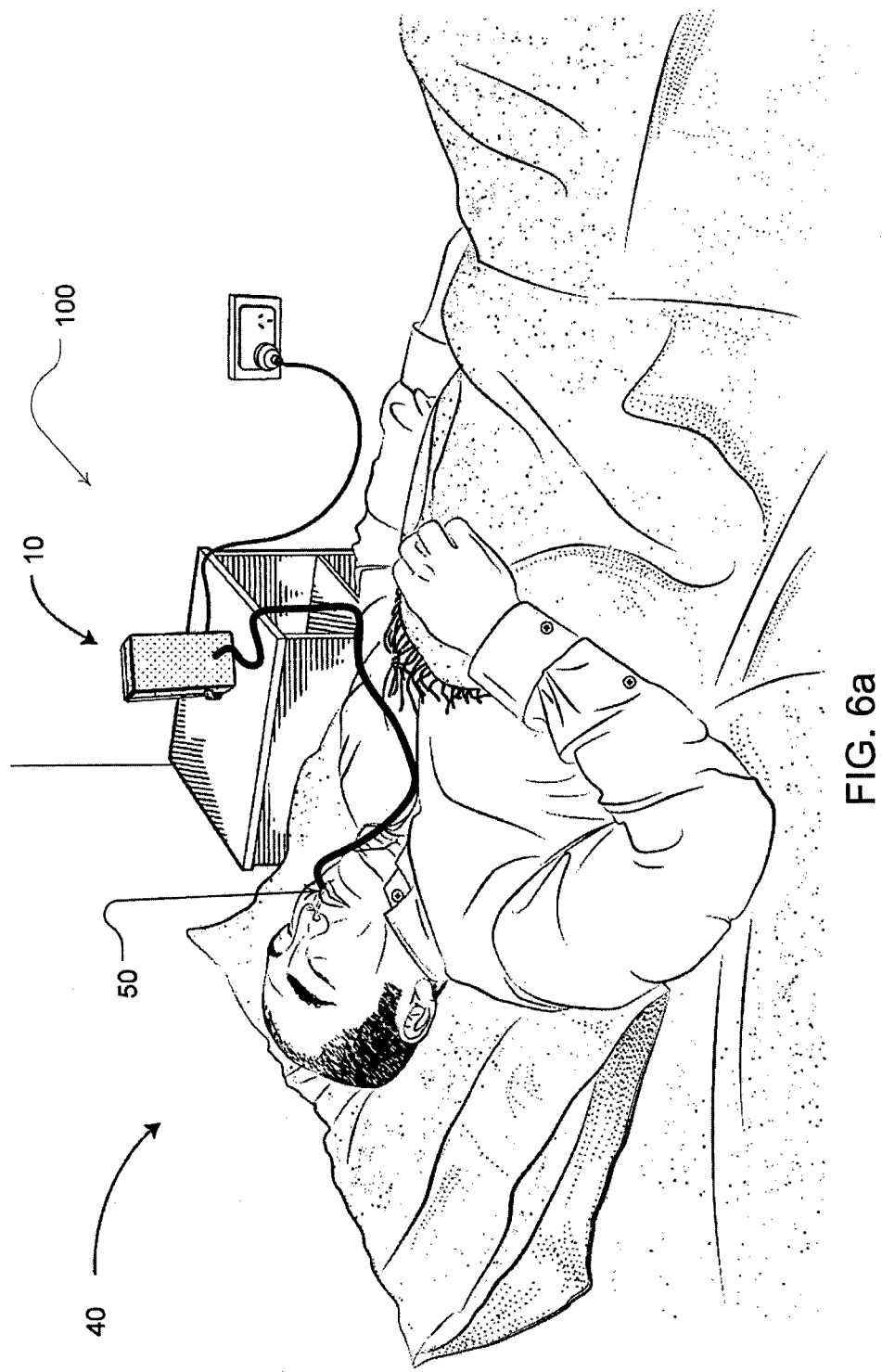

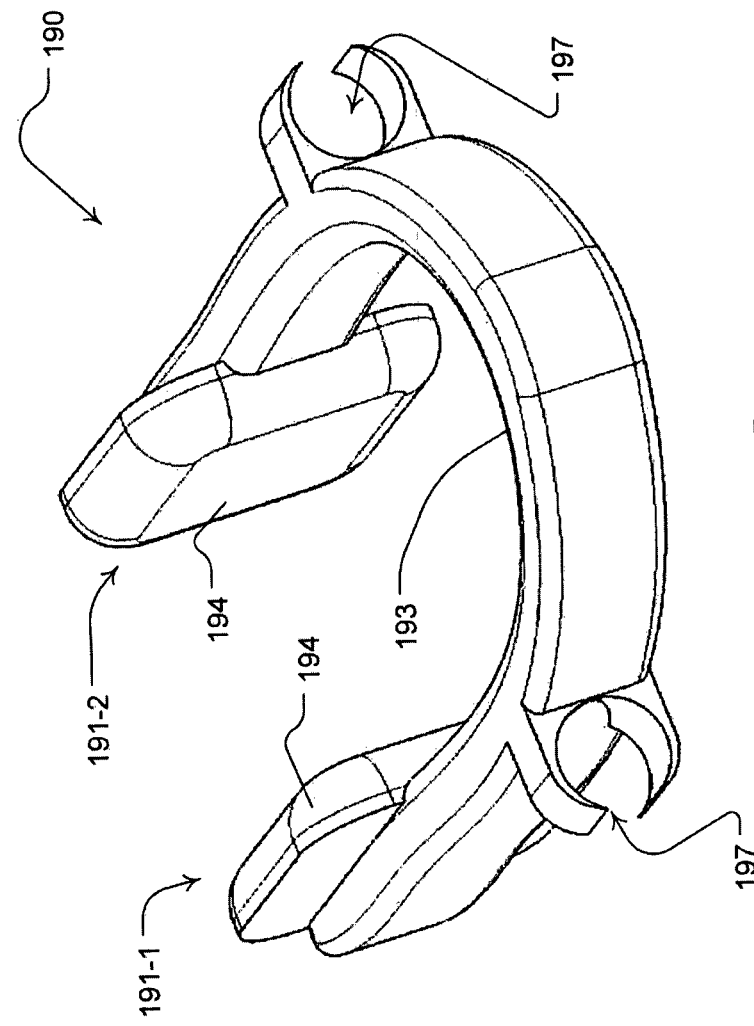
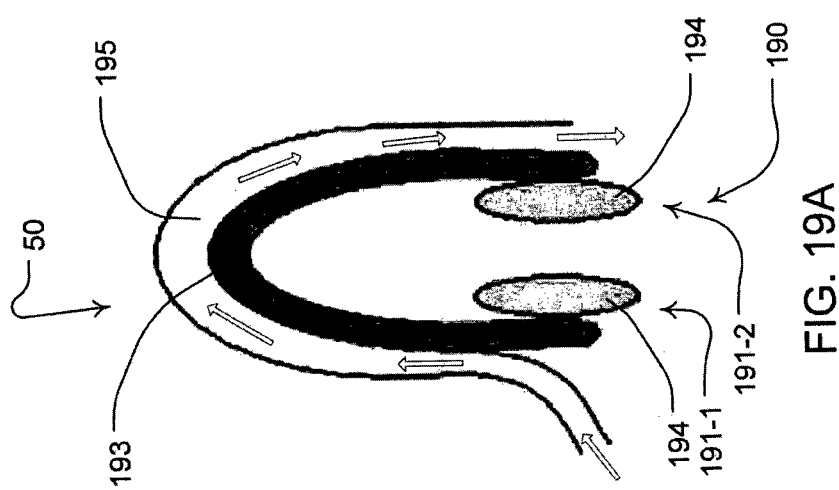
FIG. 19B
FIG. 19A

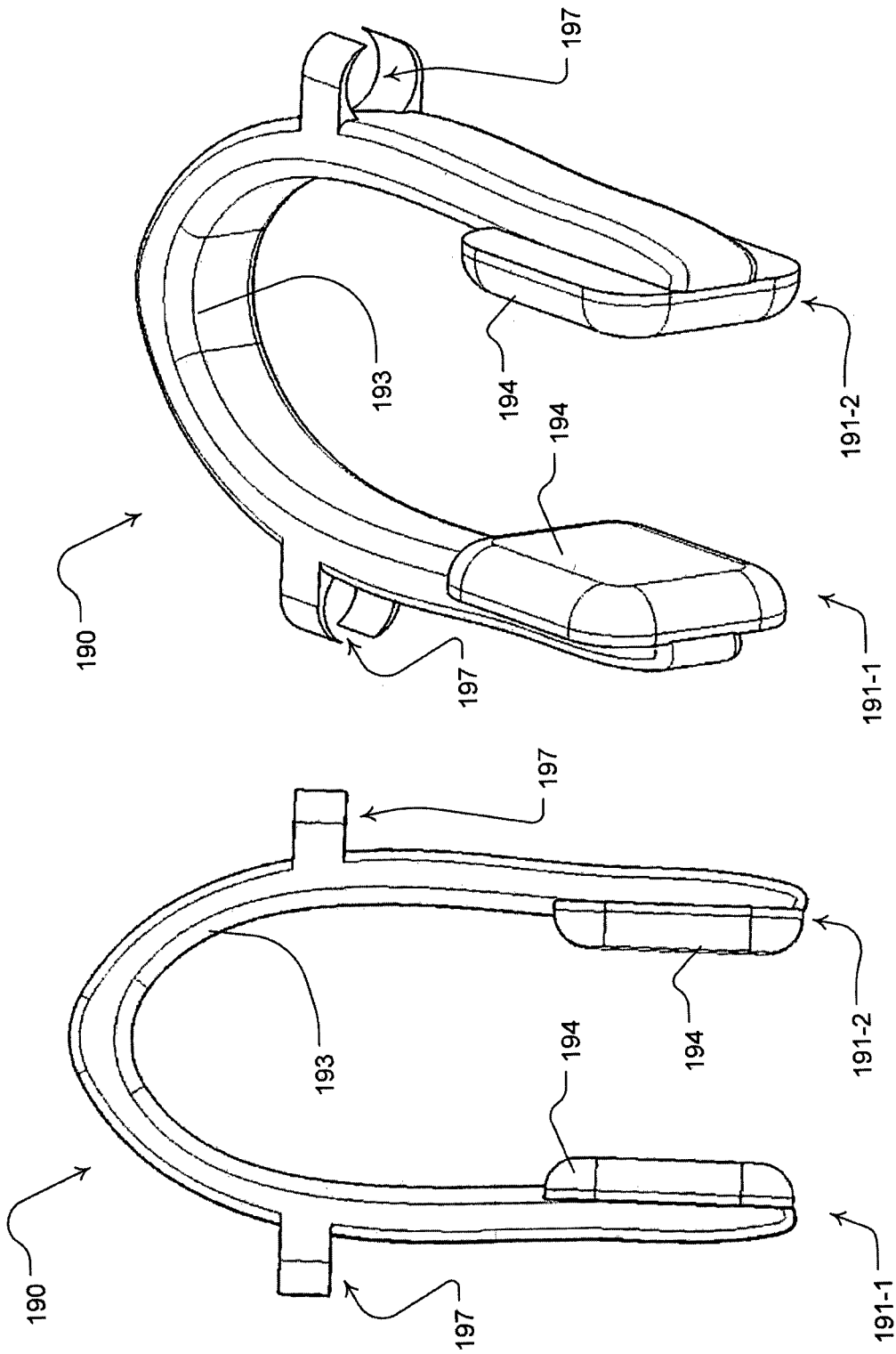

METHOD AND APPARATUS FOR ORAL FLOW THERAPY

CROSS-REFERENCE TO RELATED APPLICATIONS

The present application is a national phase entry under 35 U.S.C. § 371 of International Application No. PCT/AU2013/000445, filed April 30, 2013, published in English, which claims priority from Australia Provisional Patent Application No. 2012901699, filed Apr. 30, 2012, all of which are incorporated herein by reference.

STATEMENT REGARDING FEDERALLY SPONSORED RESEARCH OR DEVELOPMENT

Not Applicable

THE NAMES OF PARTIES TO A JOINT RESEARCH DEVELOPMENT

Not Applicable

SEQUENCE LISTING

Not Applicable

BACKGROUND OF THE INVENTION (1) Field of the Invention

The present invention relates to a method and apparatus for providing flow therapy to assist ventilation of a user. More particularly to a method and apparatus for providing an oral flow therapy to assist ventilation or reduce the work of breathing for a user.

(2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

The diagnosis of CSR usually involves conducting a sleep study and analyzing the resulting polysomnography ("PSG") data. In a full diagnostic PSG study, a range of biological parameters are monitored that typically include a nasal flow signal, measures of respiratory effort, pulse oximetry, sleeping position, and may include: electroencephalography ("EEG"), electrocardiography ("ECG"), electromyography ("EMG") and electro-oculography ("EOG"). Breathing characteristics are also identified from visual features, thus allowing a clinician to assess respiratory function during sleep and evaluate any presence of CSR. While the examination by a clinician is the most comprehensive method, it is a costly process and depends heavily upon clinical experience and understanding.

Systems

One known product used for treating sleep disordered breathing is the S9 Sleep Therapy System, manufactured by ResMed.

Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway obstruction by pushing the soft palate and tongue forward and away from the posterior oropharyngeal wall.

Non-invasive ventilation (NIV) has been used to treat CSR, OHS, COPD, MD and Chest Wall disorders. In some cases of NIV, the pressure treatment may be controlled to enforce a target ventilation by measuring a tidal volume or minute ventilation, for example, and controlling the measure of ventilation to satisfy the target ventilation. Servo-controlling of the measure of ventilation, such as by a comparison of an instantaneous measure of ventilation and a long term measure of ventilation, may serve as a treatment to counteract CSR. In some such cases, the form of the pressure treatment delivered by an apparatus may be Pressure Support ventilation. Such a pressure treatment typically provides generation of a higher level of pressure during inspiration (e.g., an IPAP) and generation of a lower level of pressure during expiration (e.g., an EPAP).

Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

PAP Device

The air at positive pressure is typically supplied to the airway of a patient by a PAP device such as a motor-driven blower. The outlet of the blower is connected via a flexible delivery conduit to a patient interface as described above.

Periodic breathing disorders of central origin, such as Cheyne-Stokes respiration, may occur together with upper airway obstruction. The oscillations in central drive to the respiratory musculature may be associated with oscillations in drive to the upper airway musculature, exacerbating any tendency to upper airway obstruction. Any method which attempts to counteract the self-sustaining oscillations in respiratory drive by ventilating the patient, typically with more ventilator drive during periods of low patient effort than during periods of high patient effort, needs the upper airway to be substantially open when it is attempting to deliver ventilatory assistance, otherwise the ventilatory assistance will be to some extent, and often totally, ineffective during the periods of low or zero patient effort, and thus unable to stabilise the patient's ventilation.

This need to keep the upper airway open is typically addressed by attempting to set an expiratory positive airway pressure (EPAP) such that the upper airway is kept open at all times. This may be achieved by some kind of iterative adjustment of EPAP while observing indicators of the patency of the airway at various EPAP levels, in a procedure called a titration. Titration is a skilled and typically expensive operation, preferably being conducted in a sleep laboratory, and may not yield an EPAP sufficient to overcome upper airway obstruction (UAO). Reasons for this include the fact that UAO is often postural, and the patient may never during the titration night assume the posture which produces the worst UAO, typically the supine posture. Sedative and other drugs may variably influence the upper airway. There is also evidence that the degree of cardiac failure affects the degree of upper airway obstruction via oedema of the upper airway. Hence an exacerbation of cardiac failure may worsen upper airway obstruction to an extent which cannot be anticipated during a titration night.

Dead Space

In mammal ventilation air or gas is passed in through the oral and/or nasal cavity to the airways for delivery to the lungs for gas exchange to occur. The airways that conduct the air or gas to the regions of the lungs where gas exchange takes place do not themselves contribute to gas exchange and consequently provide what is termed dead space. The anatomical dead space is the volume of air or gas in the conducting airways that does not take part in gas exchange. In some patients with lung disease such as emphysema, Chronic obstructive pulmonary disease (COPD), Pulmonary Embolism, Pulmonary Vasculitis, Acute respiratory distress syndrome (ARDS), Pulmonary Fibrosis or other such respiratory disorders, some of the regions of the Aveoli may no longer contribute to gas exchange. The alveolar dead space is the volume of air in the Aveoli that doesn't take part in gas exchange, due to disease. Physiological dead space is the sum of the anatomical dead space and alveolar dead space. There is a relationship between the volume of dead space and the work required to achieve a particular level of alveolar ventilation. In certain disease states dead space can be abnormally high leading to, or exacerbating respiratory problems and increasing the work of breathing.

BRIEF SUMMARY OF THE TECHNOLOGY

One aspect of the present technology relates to a device for providing oral therapy to assist ventilation of a user.

Another aspect of the present technology relates to a method for treating a respiratory disorder, a lung disease or respiratory insufficiency disorder.

Another aspect of the present technology relates to an apparatus for providing an oral flow therapy to treat a respiratory disorder, a lung disease or respiratory insufficiency disorder.

Another aspect of the present technology relates to an apparatus for providing a constant oral flow therapy to treat a respiratory disorder, a lung disease or respiratory insufficiency disorder.

Another aspect of the present technology relates to an apparatus for providing a constant oral flow therapy with provision for a pressure limit to allow oral obstruction such as in deglutition, or nasal obstruction.

Another aspect of the present technology relates to a respiratory therapy system with a sealed oral interface.

Another aspect of the present technology relates to a method for reducing the dead space in a patient having a respiratory disorder, a lung disease or respiratory insufficiency disorder.

Another aspect of the present technology relates to an apparatus for providing a therapy to reduce a user's dead space.

Another aspect of the present technology relates to a respiratory therapy system having a sealed interface configured to wash out a user's nasal and/or oral dead space. The sealed interface may include an oral interface or a nasal interface.

Another aspect of the present technology includes a method of supplying a volume of breathable gas into a user's respiratory system via a sealed oral interface, wherein the breathable gas flushes out residual expired air in the oral and/or nasal cavities to assist in reducing the amount of dead space.

Another aspect of the present technology include a device comprising a source of breathable gas, an oral interface and a controller to control the delivery of a supply of breathable gas to the oral interface. The oral interface being configured to sealingly couple to a user's mouth to provide sealed communication to the oral cavity. The controller is configured to provide a volume or flow rate of breathable gas to the oral interface to assist in washing out the oral and/or nasal cavities to reduce the work of breathing.

Another aspect of the present technology relates to a respiratory therapy system comprising a control system adapted to control the delivery of a volume or flow rate of a gas or air to a user via a sealed oral interface.

Another aspect of the present technology relates to a respiratory therapy system comprising a control system adapted to control the delivery of a pressurized flow of a gas or air to a user via a sealed oral interface.

Another aspect of the present technology relates to an algorithm configured to synchronize the delivery of a volume of gas with a user's respiratory system.

Another aspect of the present technology relates to an algorithm configured to synchronize the delivery of a volume of gas during a portion of the respiratory cycle.

Another aspect of the present technology relates to an algorithm configured to synchronize the delivery of a volume of gas at the end of each expiratory cycle.

Other aspects, features, and advantages of the present technology will become apparent from the following detailed description when taken in conjunction with the accompanying drawings, which are a part of this disclosure and which illustrate, by way of example, principles of this technology.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

Treatment Systems

Therapy

Respiratory System

Figure 2A:
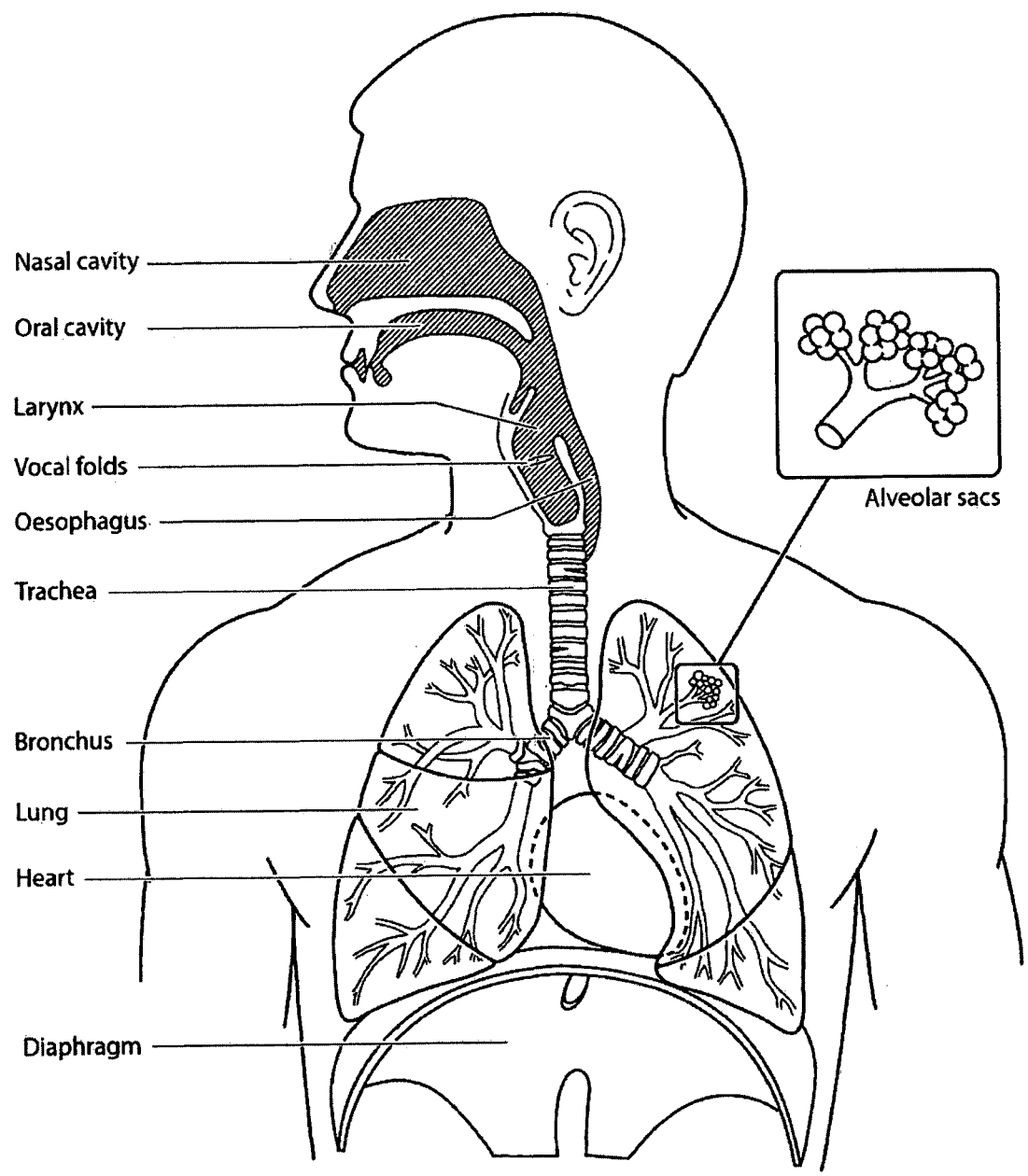

FIG. 2a shows an overview of a human respiratory system including the nasal and oral cavities, the larynx, vocal folds, oesophagus, trachea, bronchus, lung, alveolar sacs, heart and diaphragm.

Figure 2B:
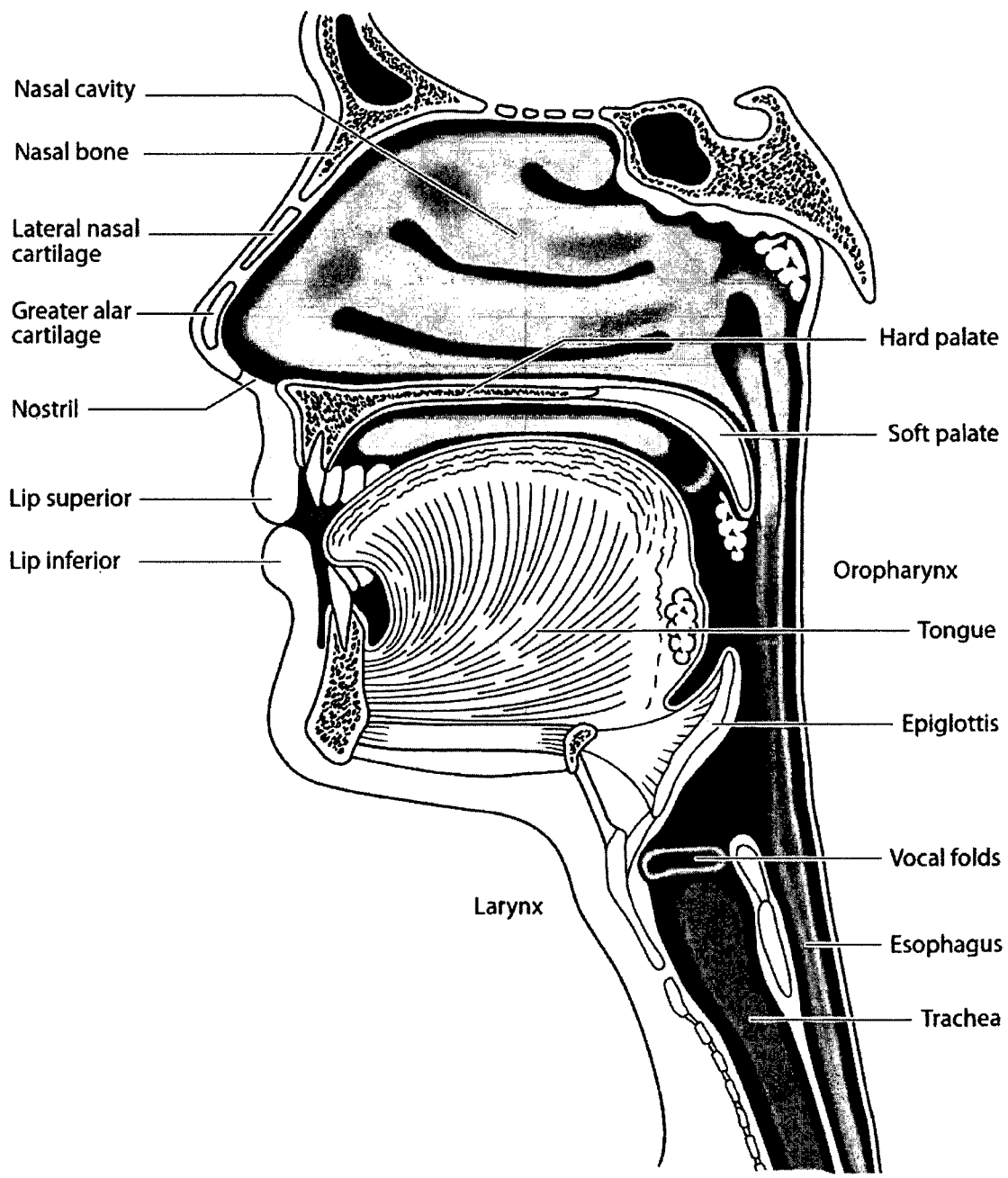

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Patient Interface

Figure 3A:
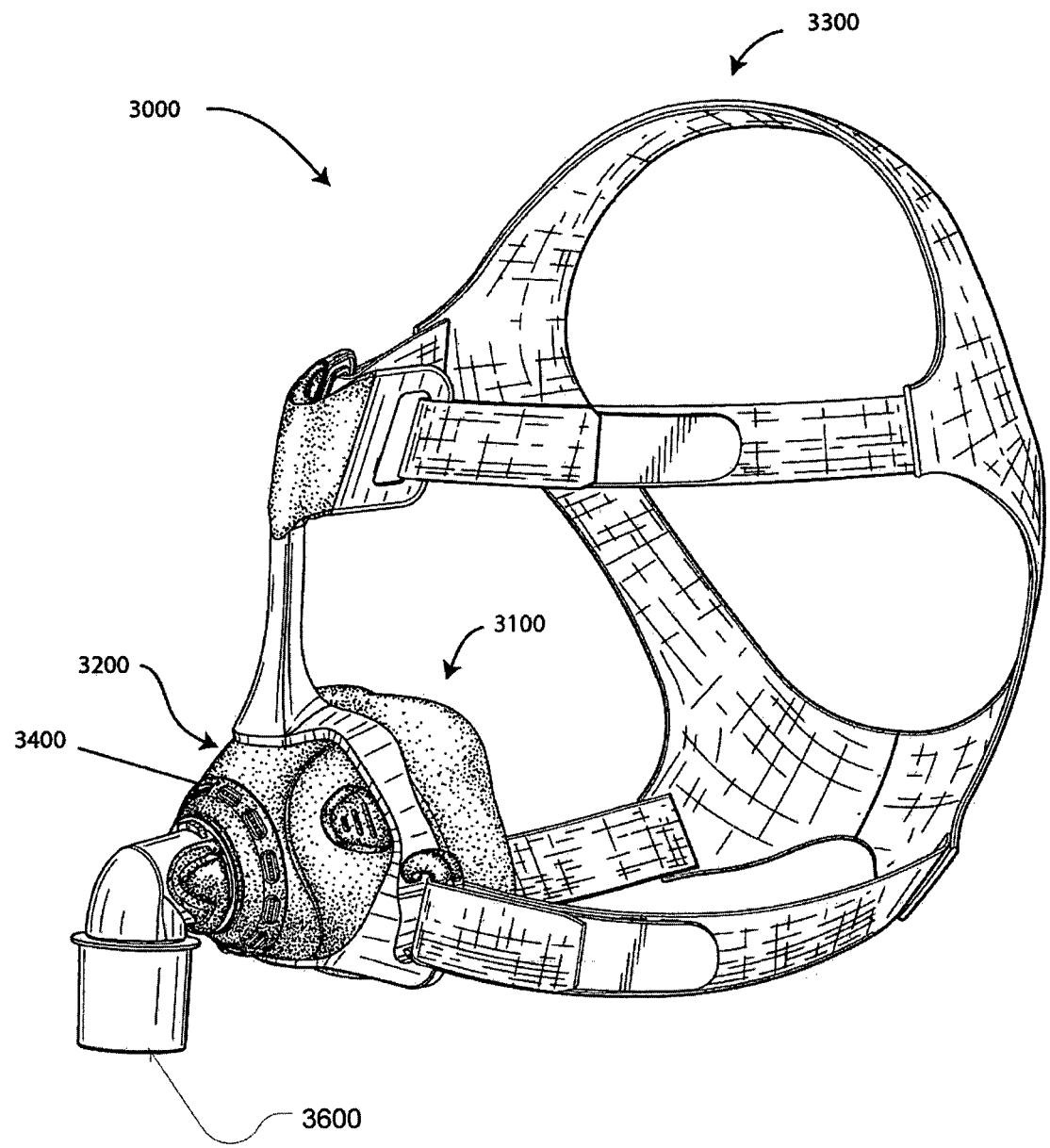

FIG. 3a shows a traditional mask-type patient interface.

PAP Device

Figure 4A:
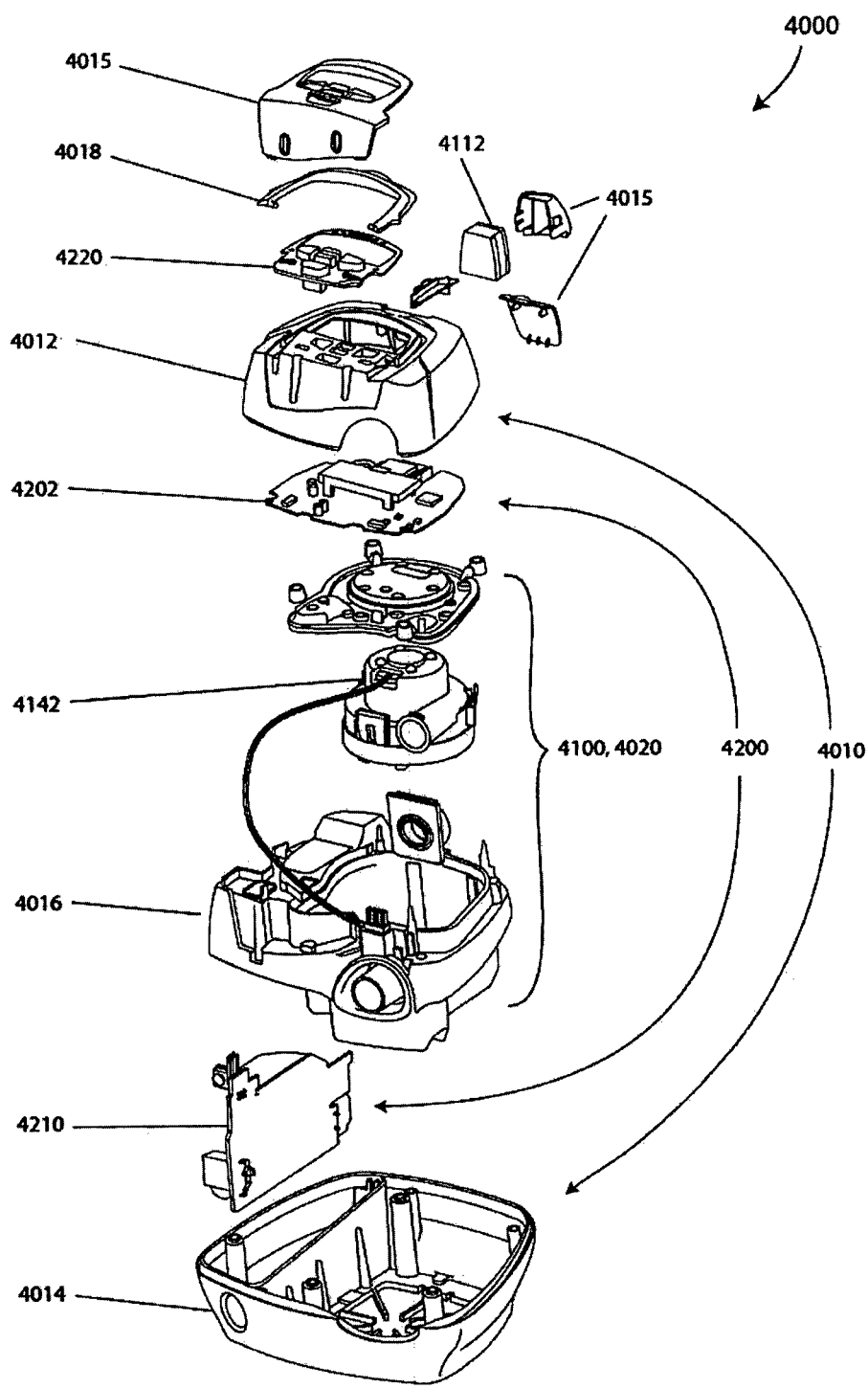

FIG. 4a shows a PAP device in exploded view in accordance with one form of the present technology.

Figure 4B:
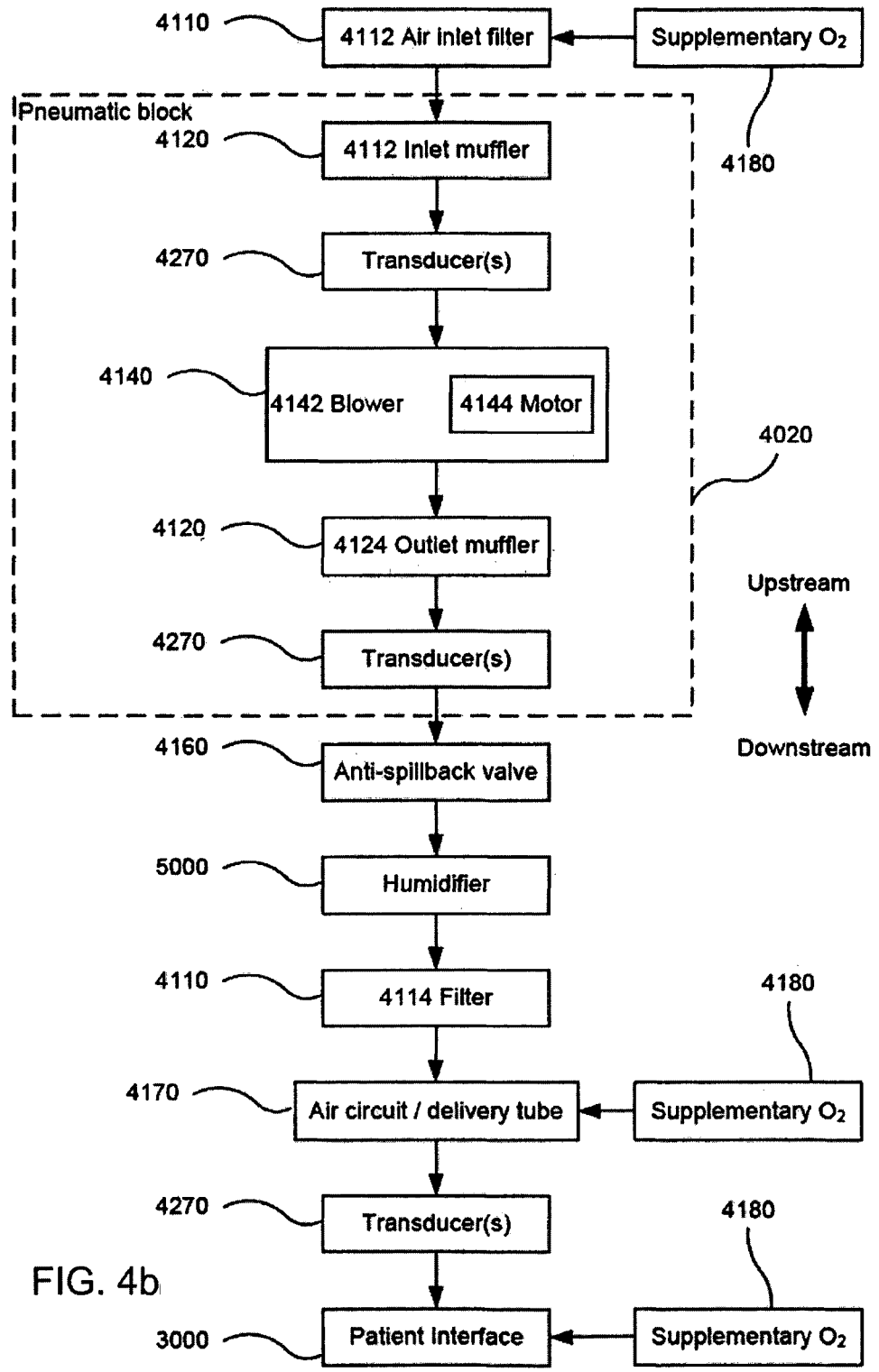

FIG. 4b shows a schematic diagram of the pneumatic circuit of an example PAP device of FIG. 4a. The directions of upstream and downstream are indicated.

Figure 4C:
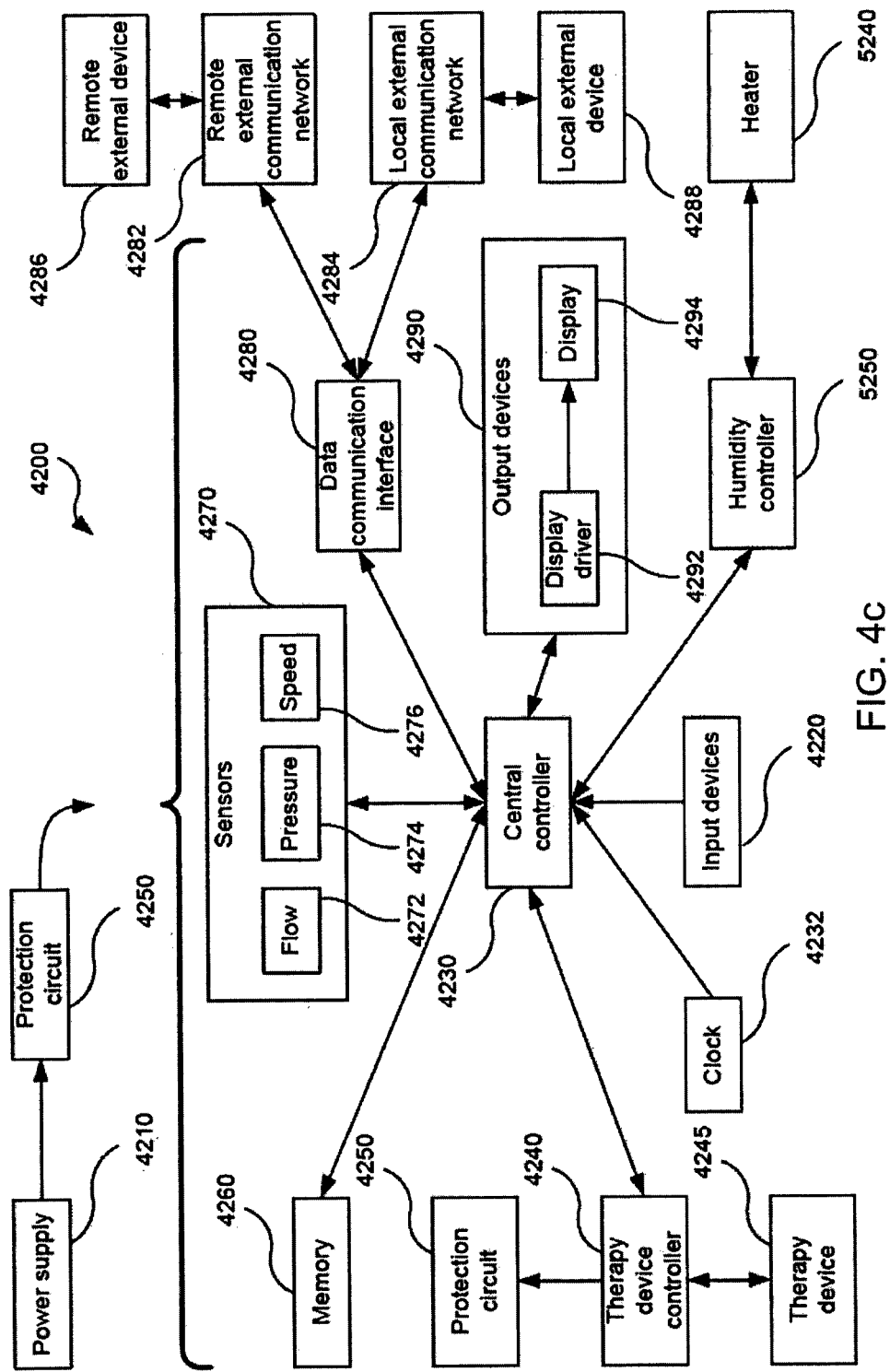

FIG. 4c shows a schematic diagram of example electrical components of the PAP device of FIG. 4a.

Humidifier

Figure 5A:
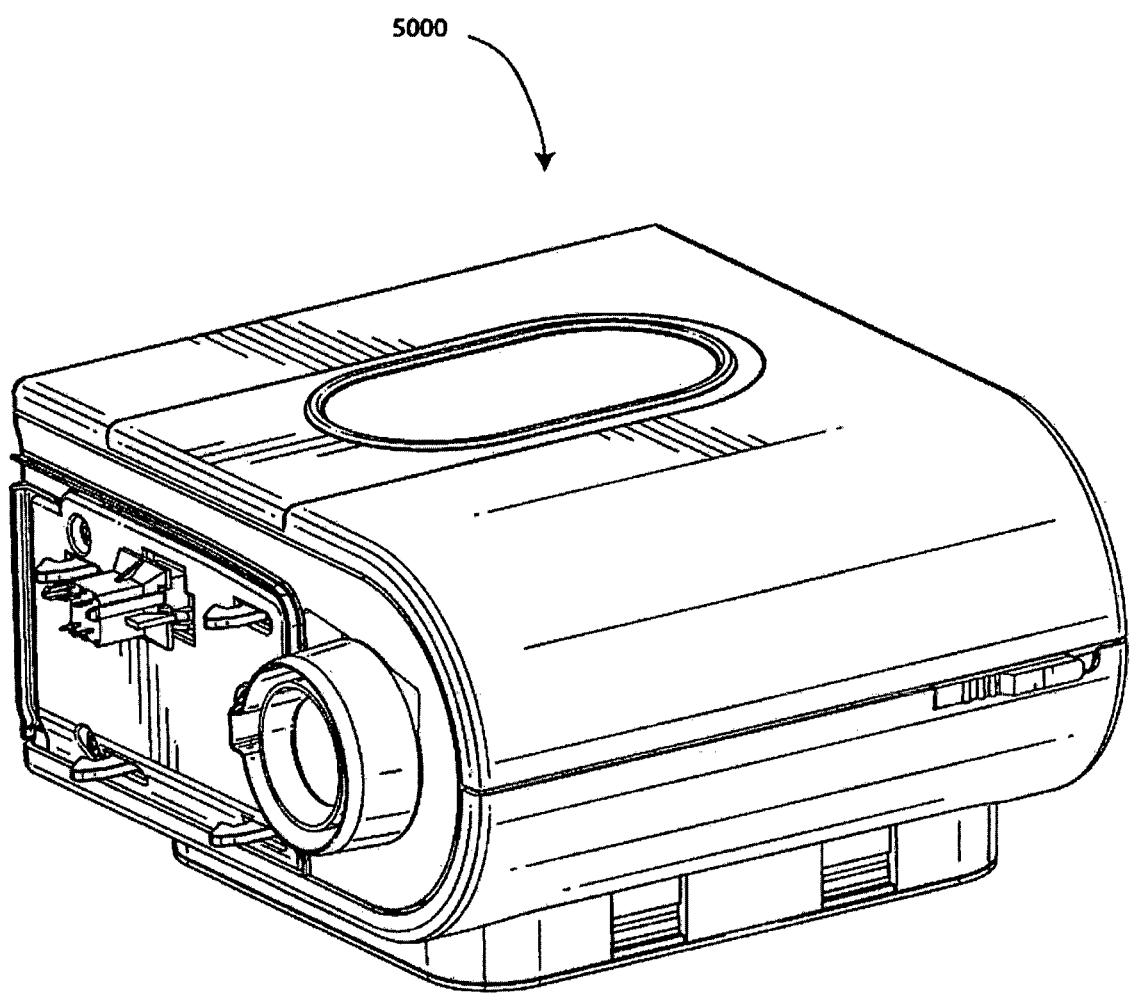

FIG. 5a shows a traditional humidifier in accordance with one aspect of the present technology.

Oral System

FIG. 6a is an illustration of a PAP device implemented as an oral therapy system in accordance with some embodiments of the present technology.

Figure 6B:
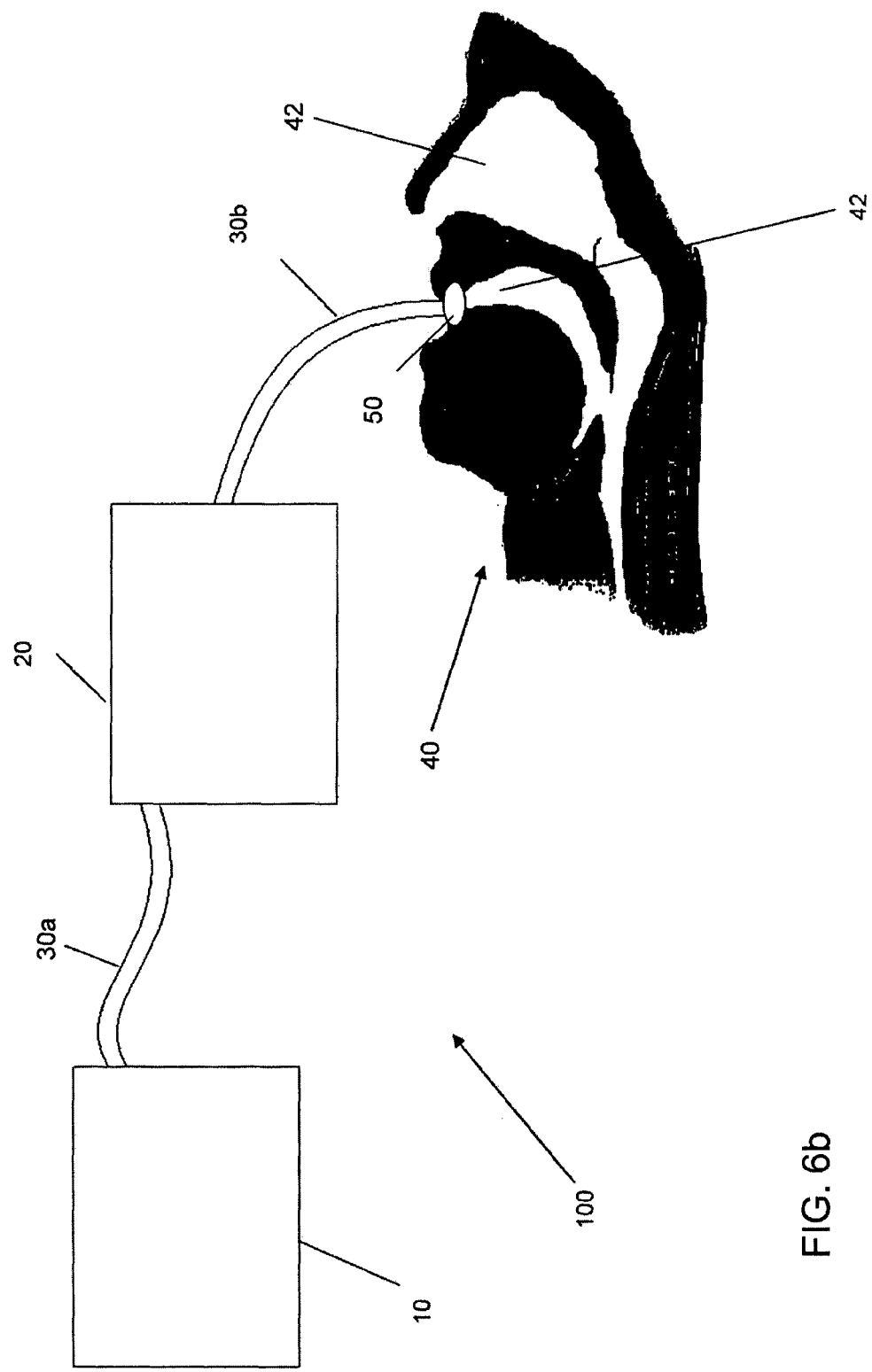

FIG. 6b is a schematic illustrating an oral system according to the present technology.

Figure 7:
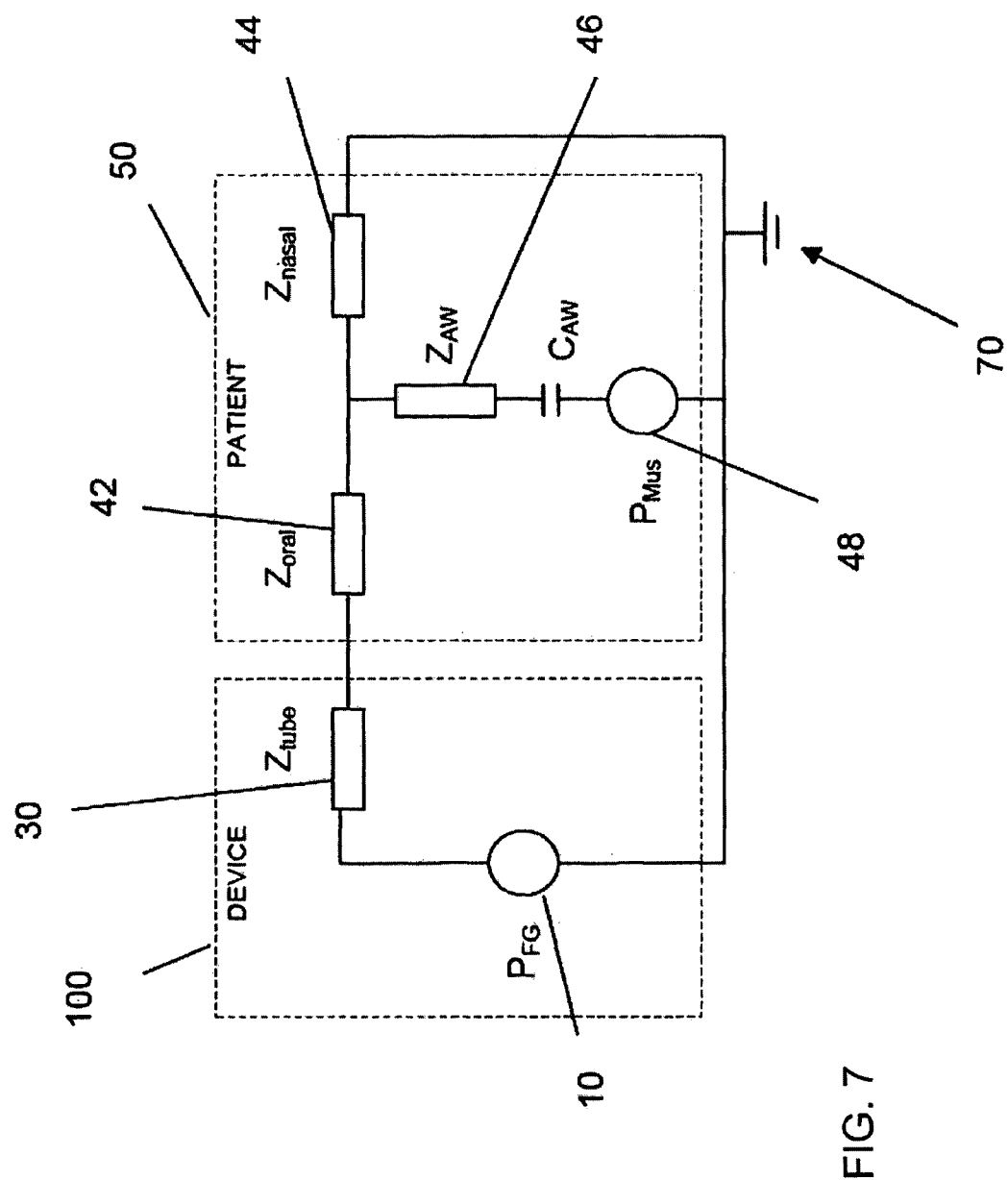

FIG. 7 is an electro-pneumatic analogue model of a therapy system according to the present technology.

Figure 8:
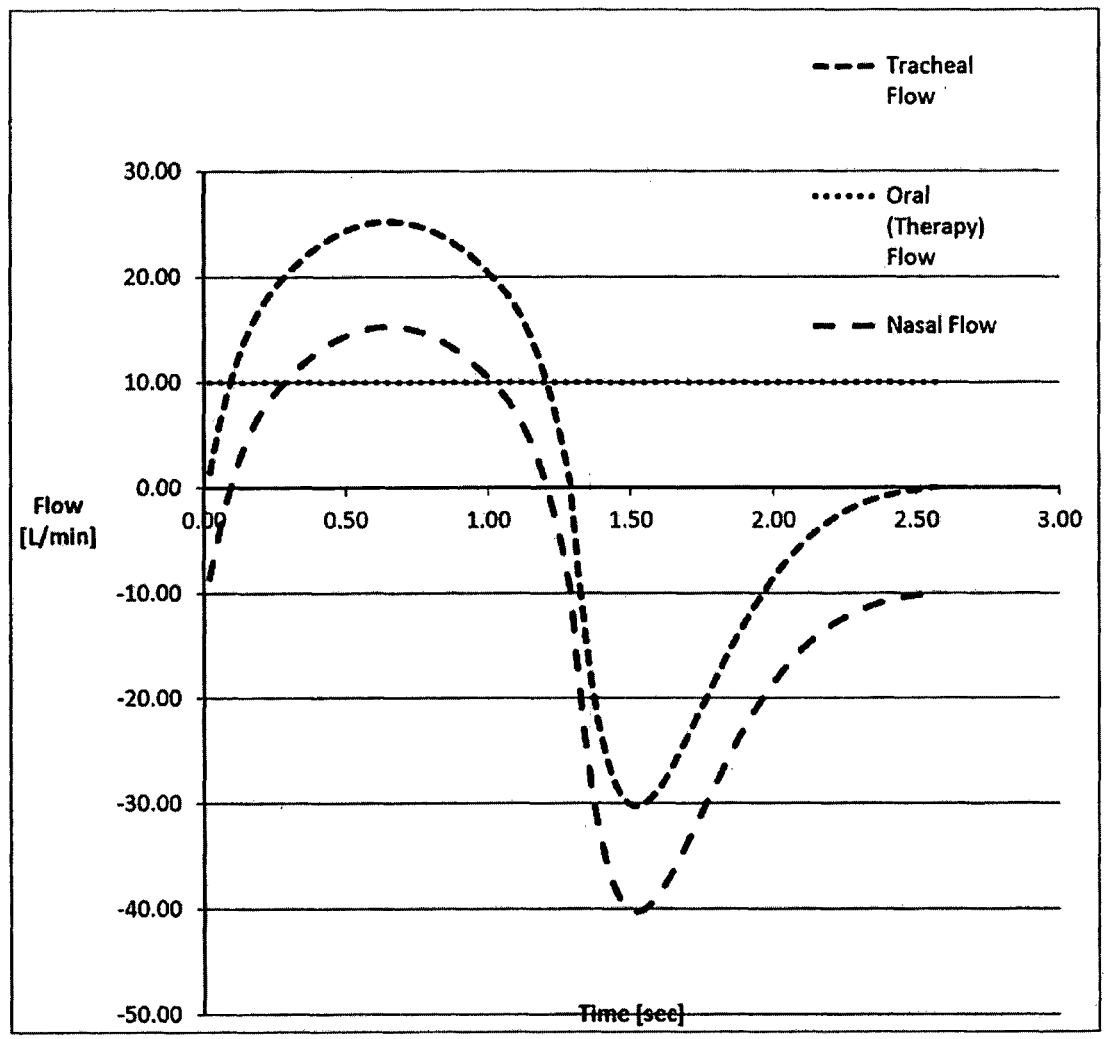

FIG. 8 is a graphical representation of a constant flow therapy provided according to an example of the present technology.

Figure 9:
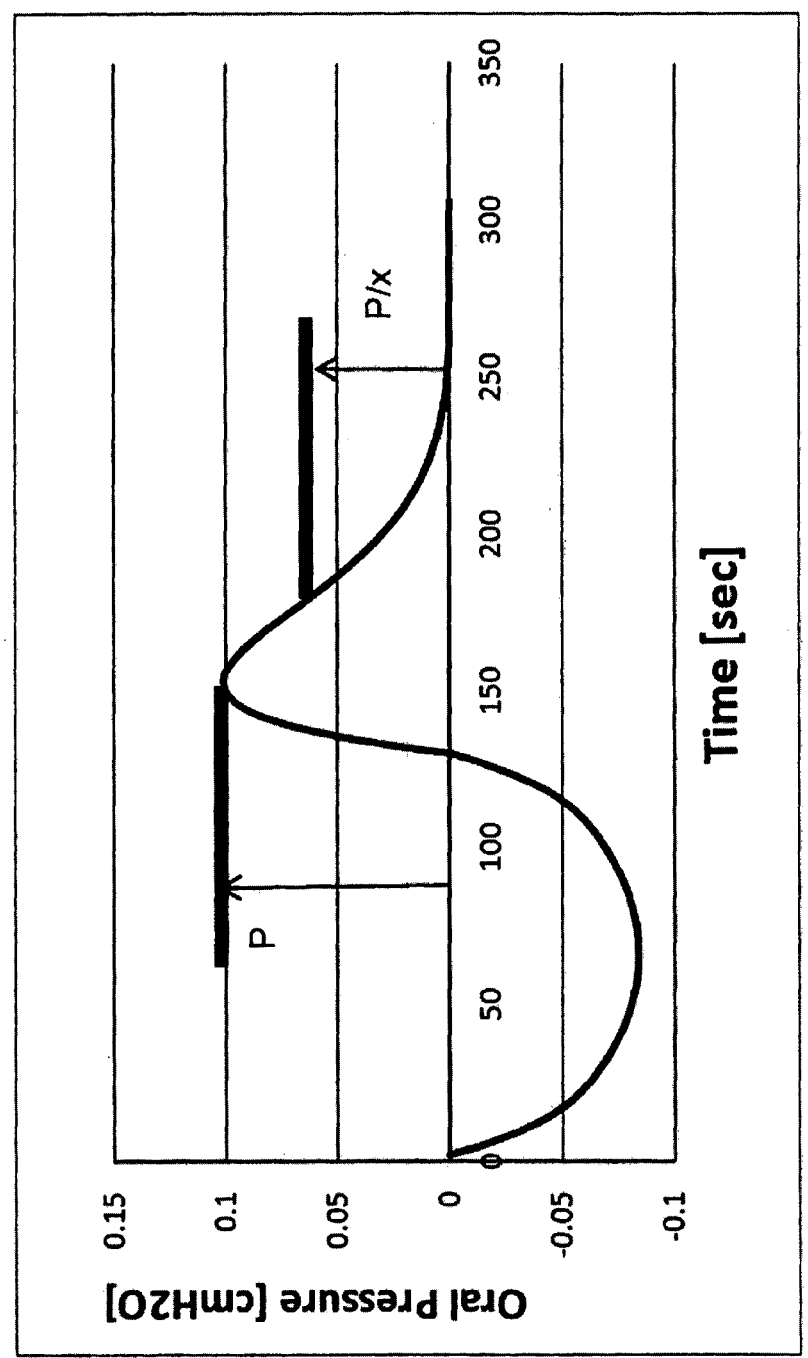

FIG. 9 is a graphical representation of the oral pressure during a single respiratory breath.

Figure 10:
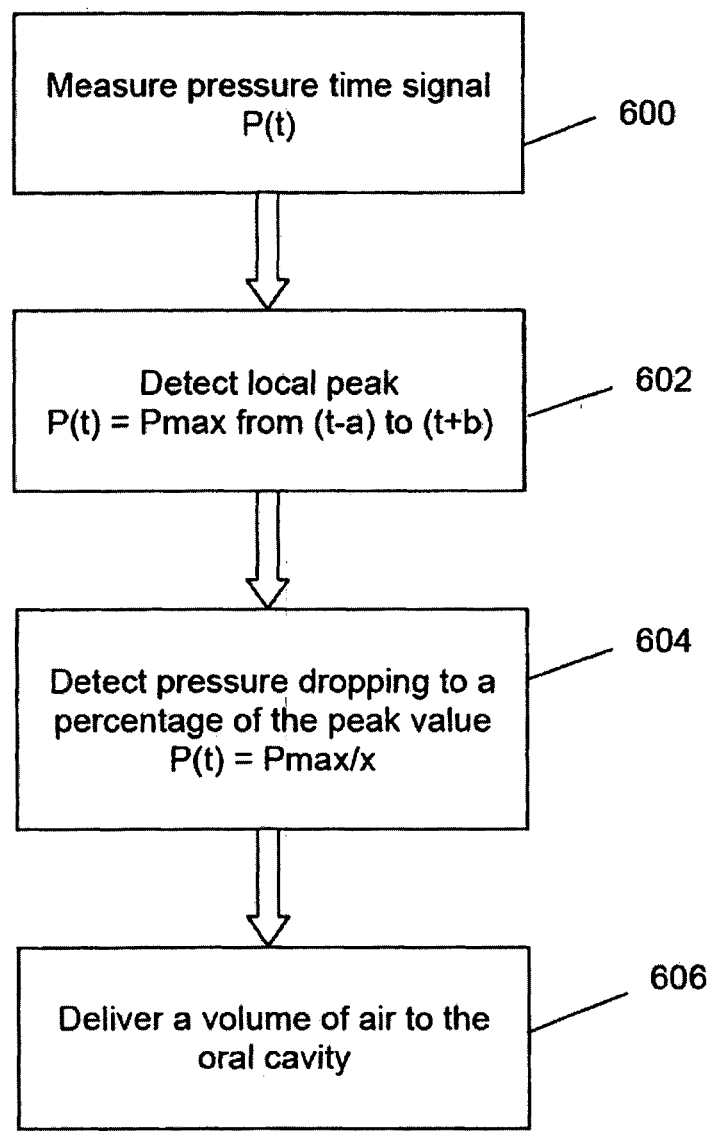

FIG. 10 is a graphical representation of an oral flow therapy provided according to an example of the present technology.

Figure 11:
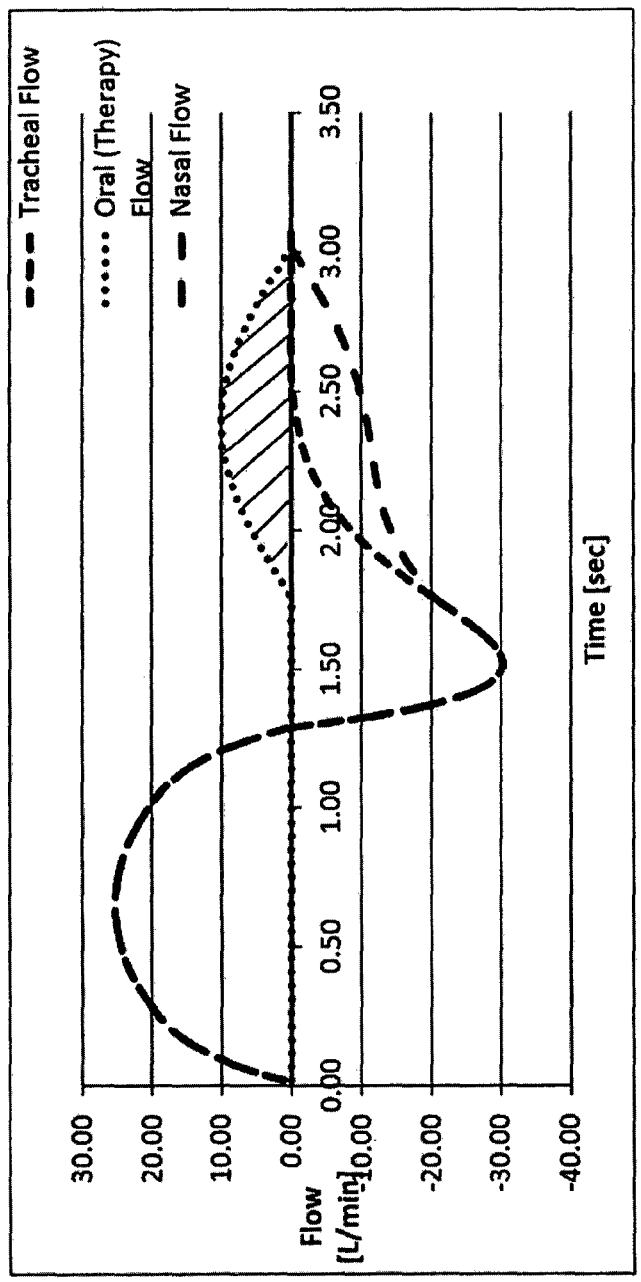

FIG. 11 is a flow diagram of a control system according to an example of the present technology.

Figure 12:
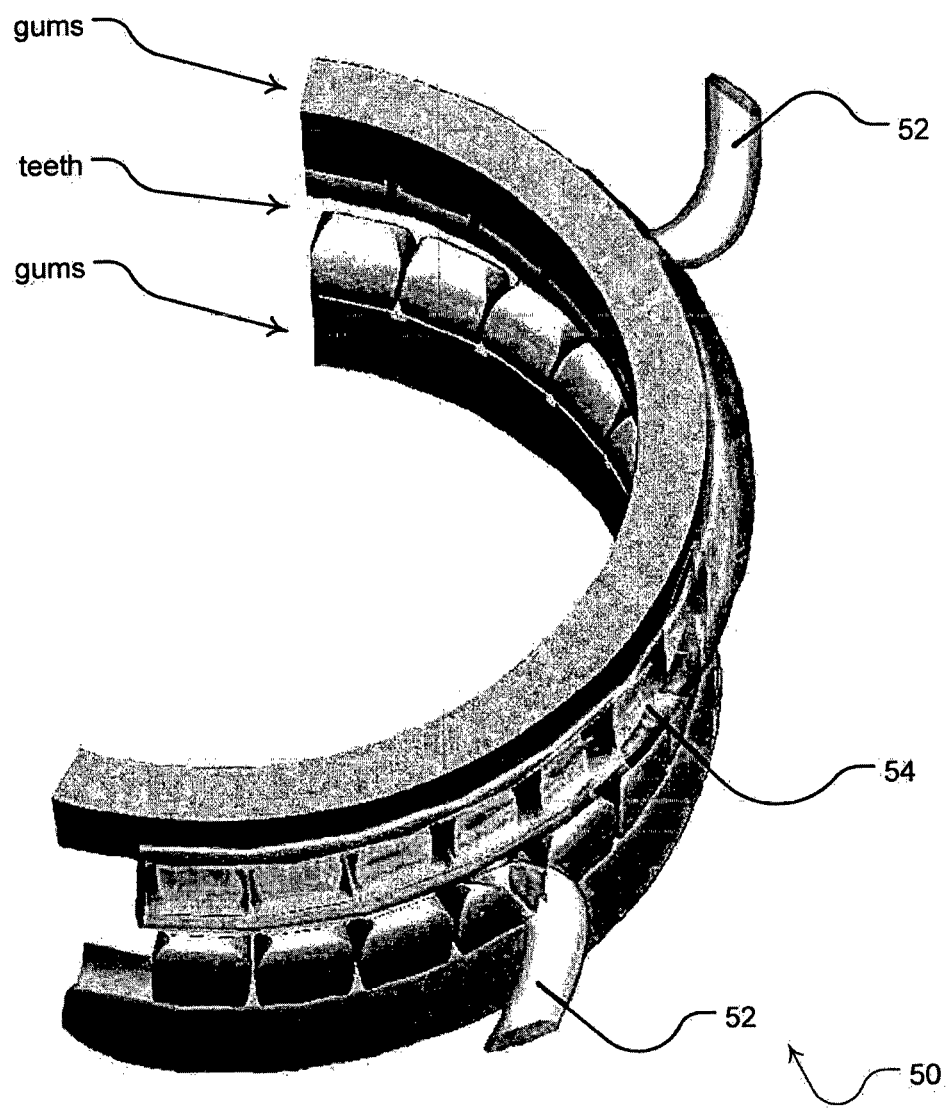

FIG. 12 is an example of an oral interface device according to the present technology.

Figure 13:
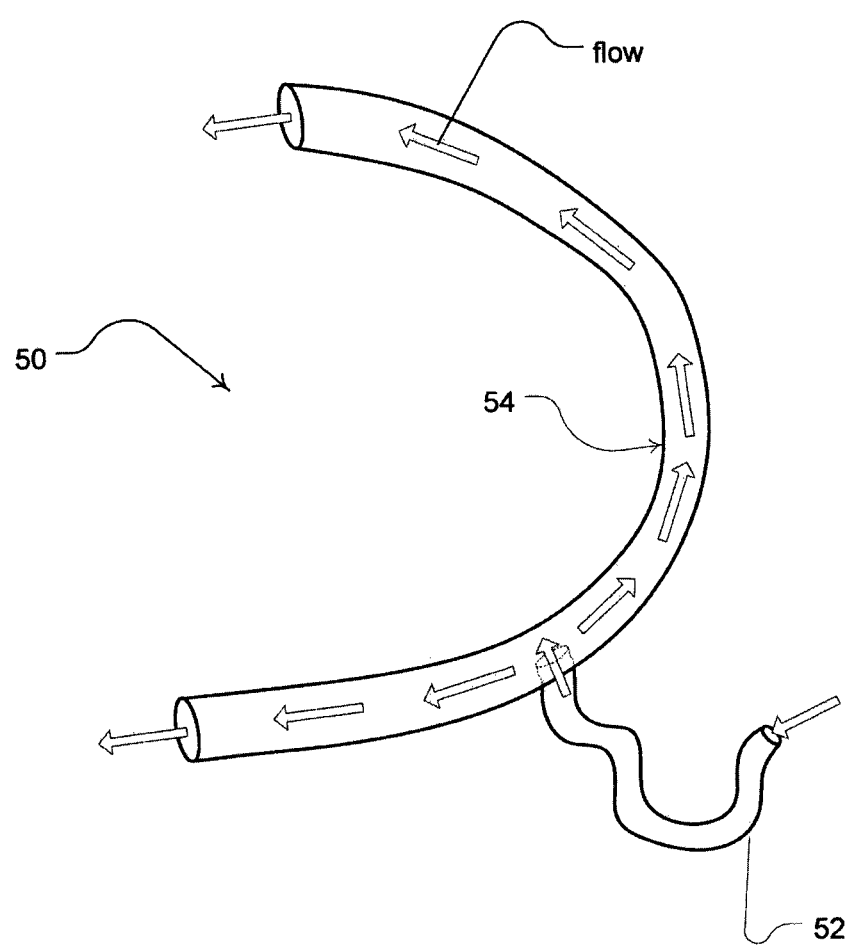

FIG. 13 is an illustration of a further example oral interface device having a single supply conduit.

Figure 14:
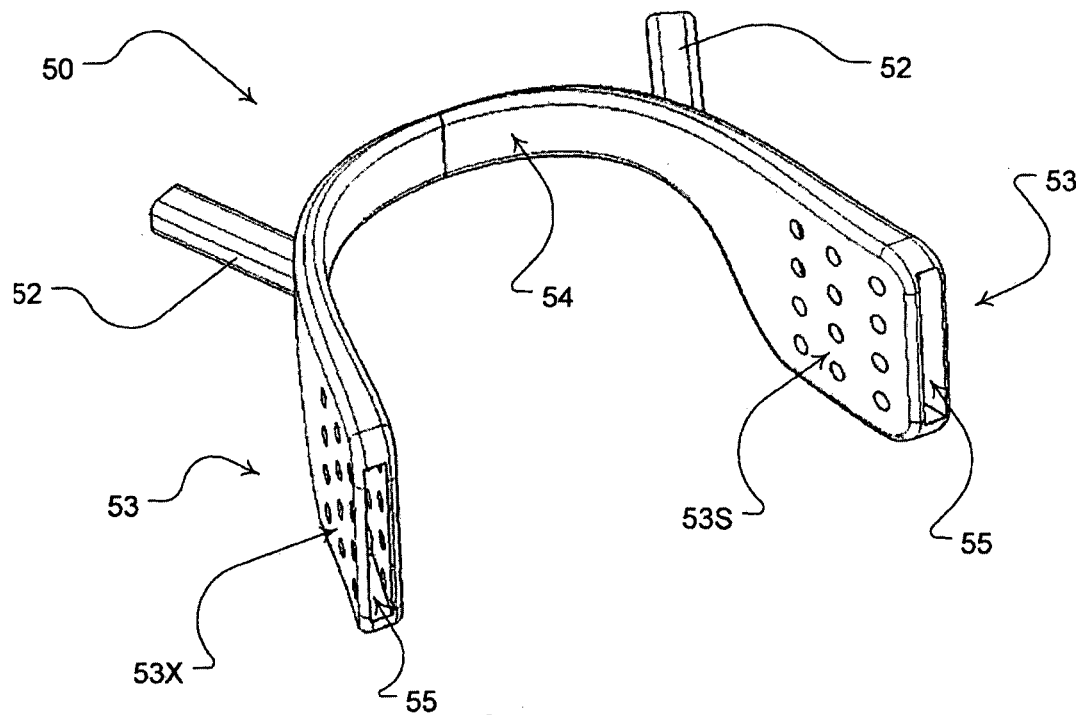
Figure 15:
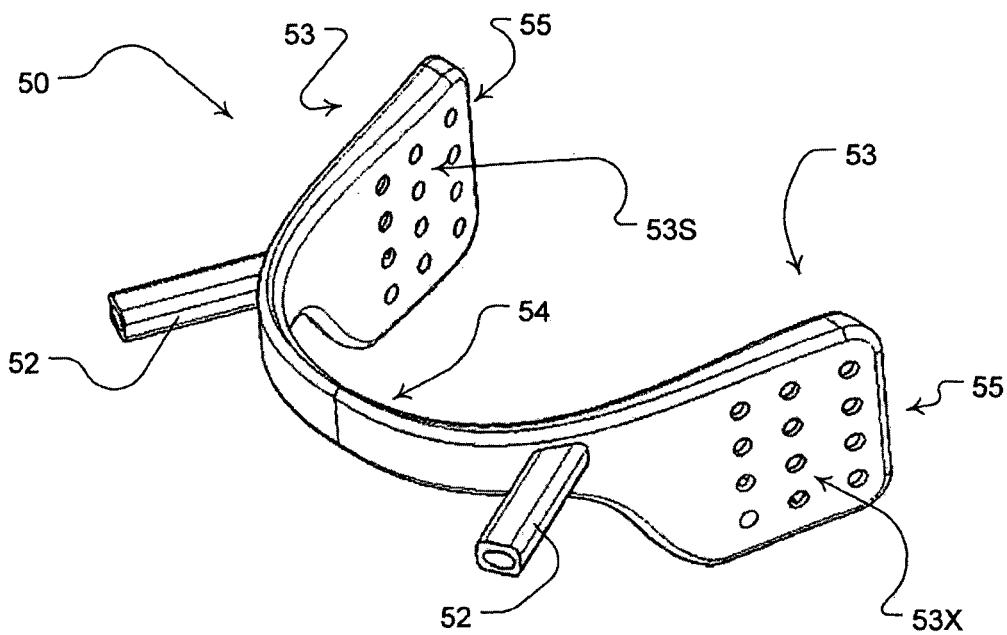

FIGS. 14 and 15 show another example oral interface device with dual supply conduits.

Figure 16:
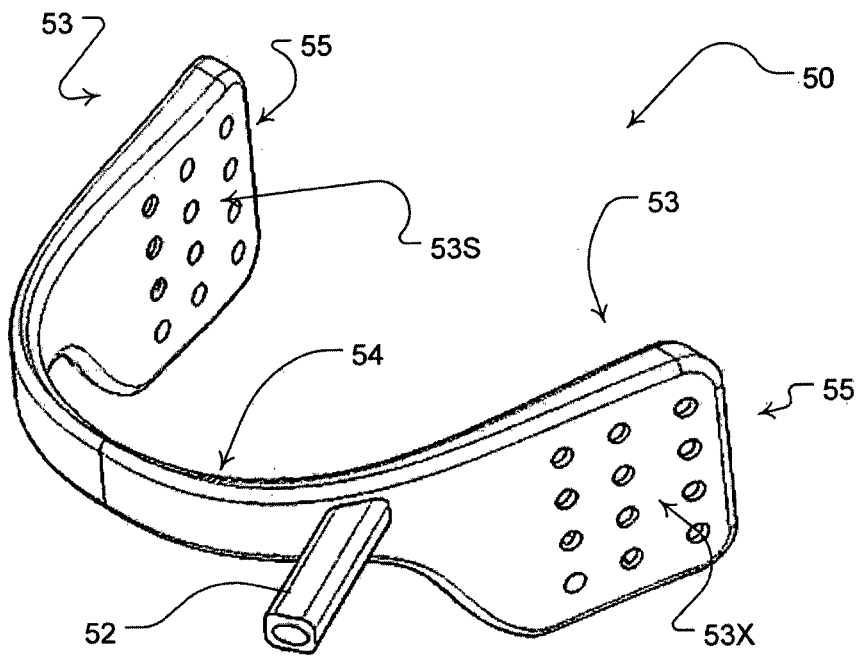

FIG. 16 is an illustration of an oral interface device having a single supply conduit.

Figure 17:
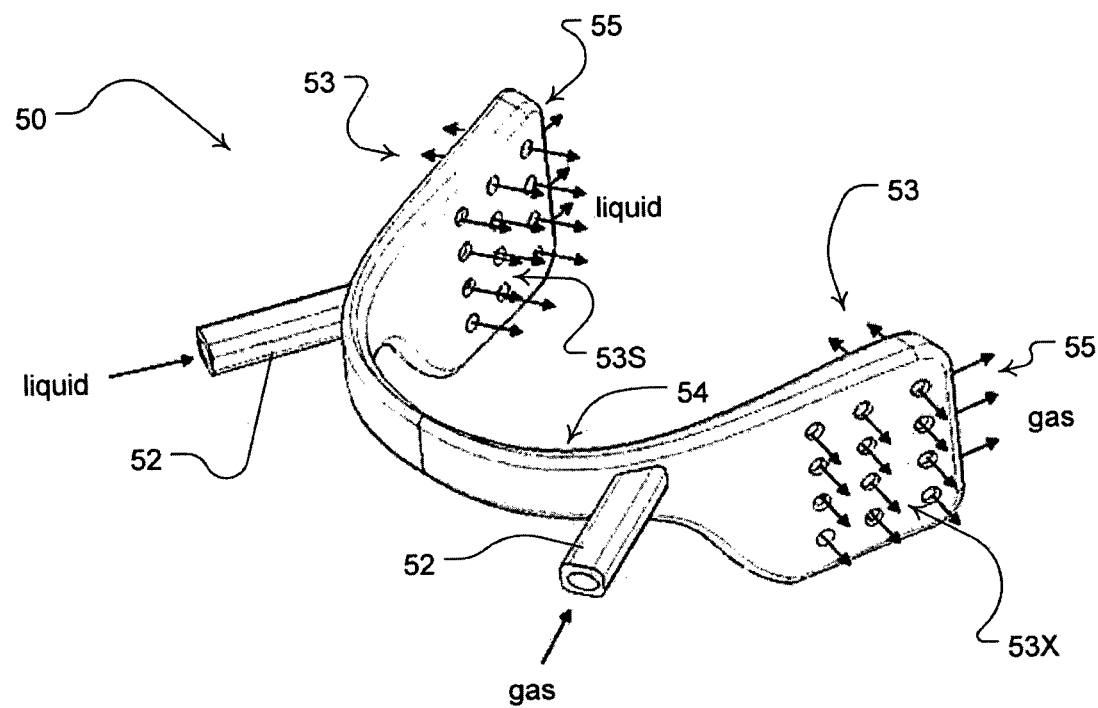

FIG. 17 is an illustration of an oral interface device having gas and water supply conduits.

Figure 18:
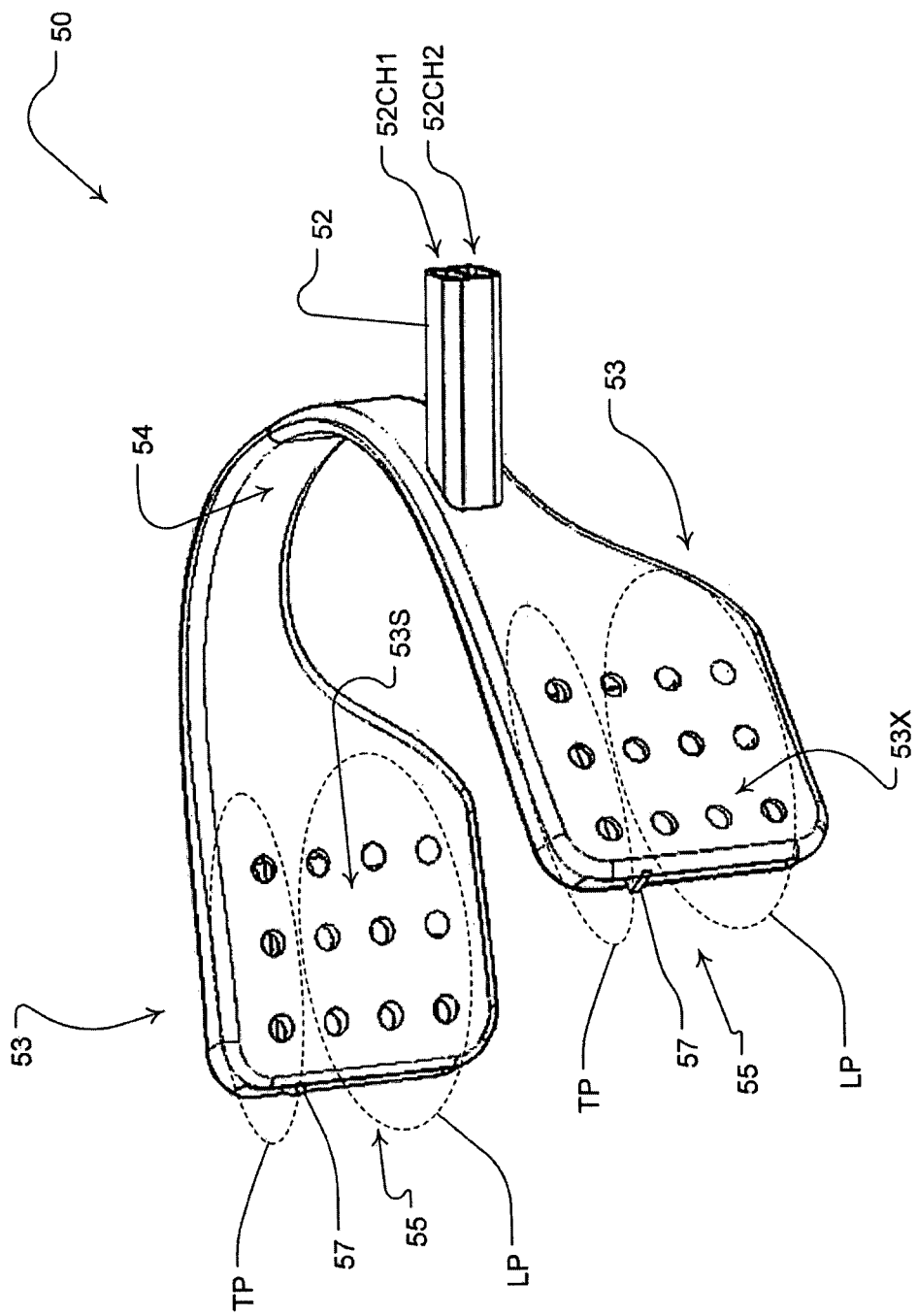

FIG. 18 is an illustration of an oral interface device employing a single dual channel supply conduit for both water and gas supply.

Figure 19:
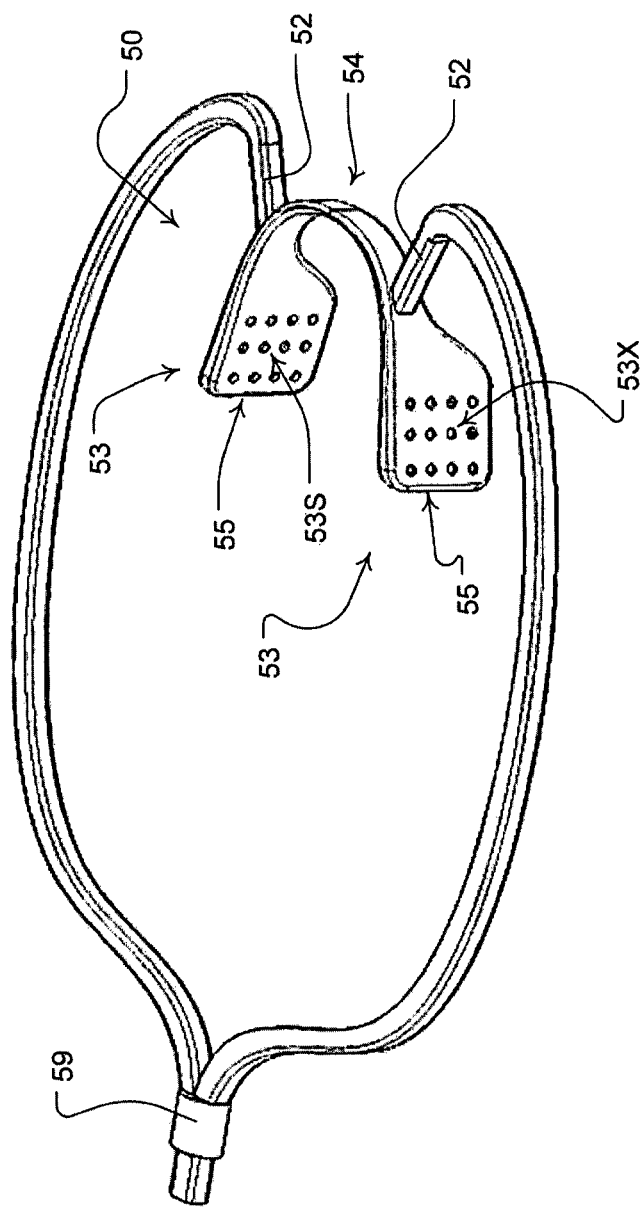

FIG. 19 shows an oral interface device employing a delivery tube connector.

FIG. 19A is an illustration of an oral interface with a retaining clip for use with some embodiments of the present technology.

FIGS. 19B, 19C and 19D show various views of a further example retaining clip for implementation with some embodiments of the present technology.

Figure 20:
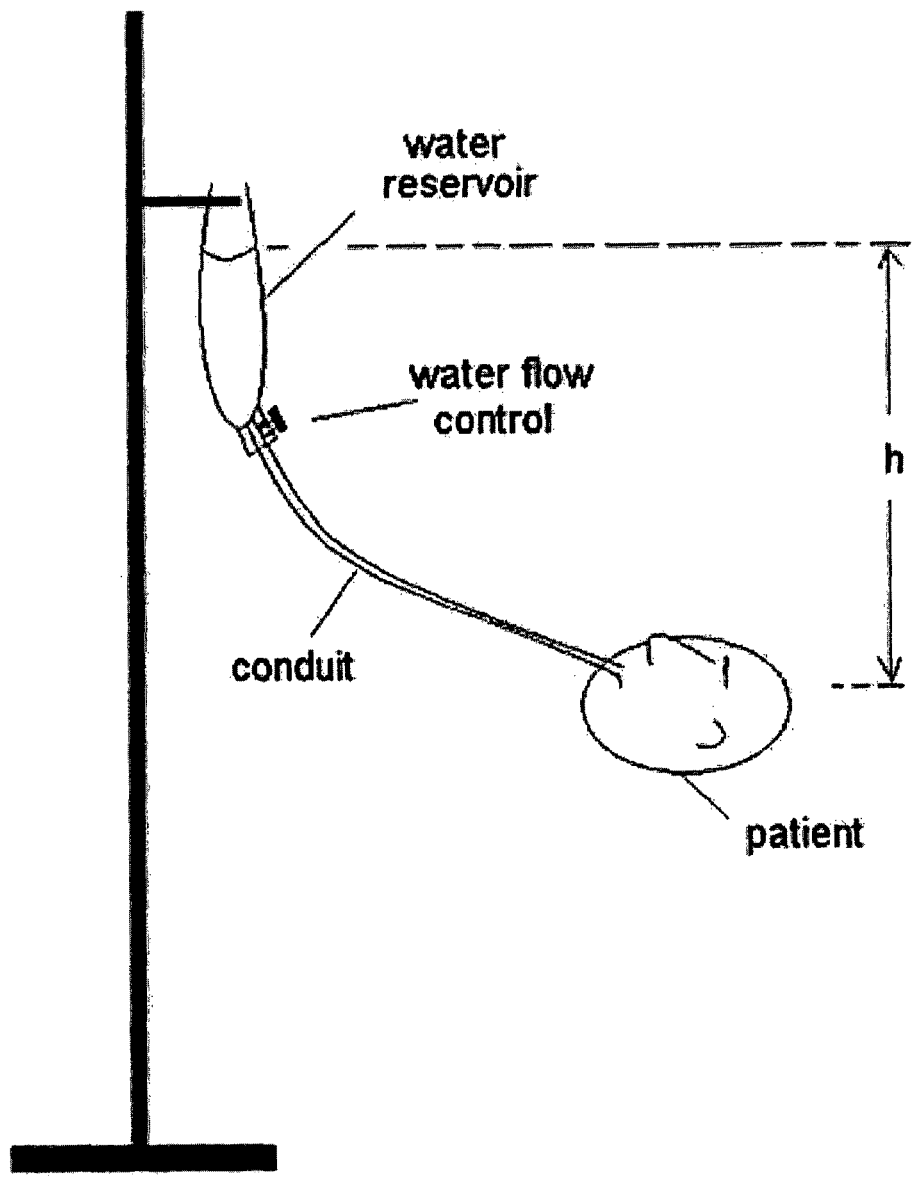

FIG. 20 is an illustration of a gravity feed water supply for some humidification embodiments of the present technology.

Figure 21:
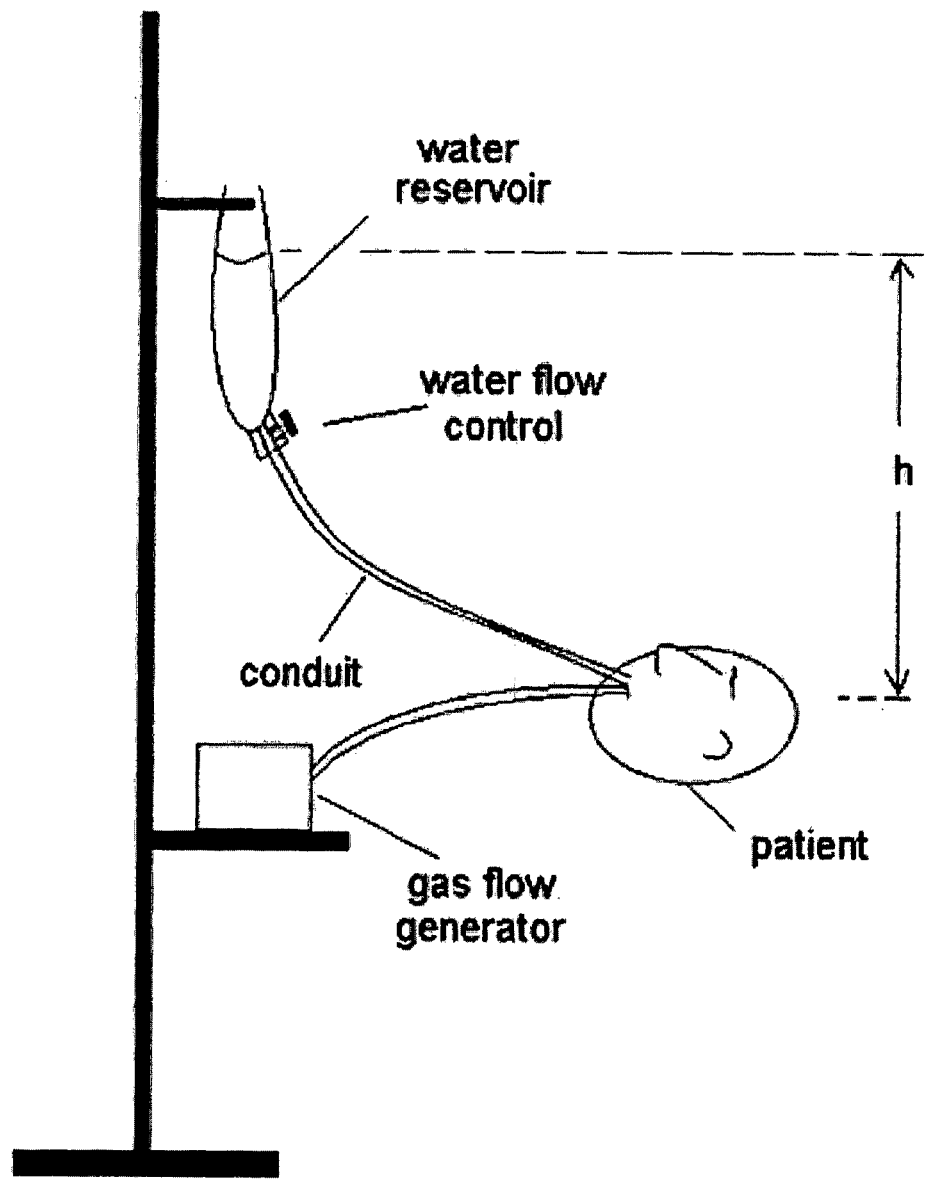

FIG. 21 is an illustration of a gravity feed water supply and gas flow generator for some embodiments of the present technology.

Figure 22:
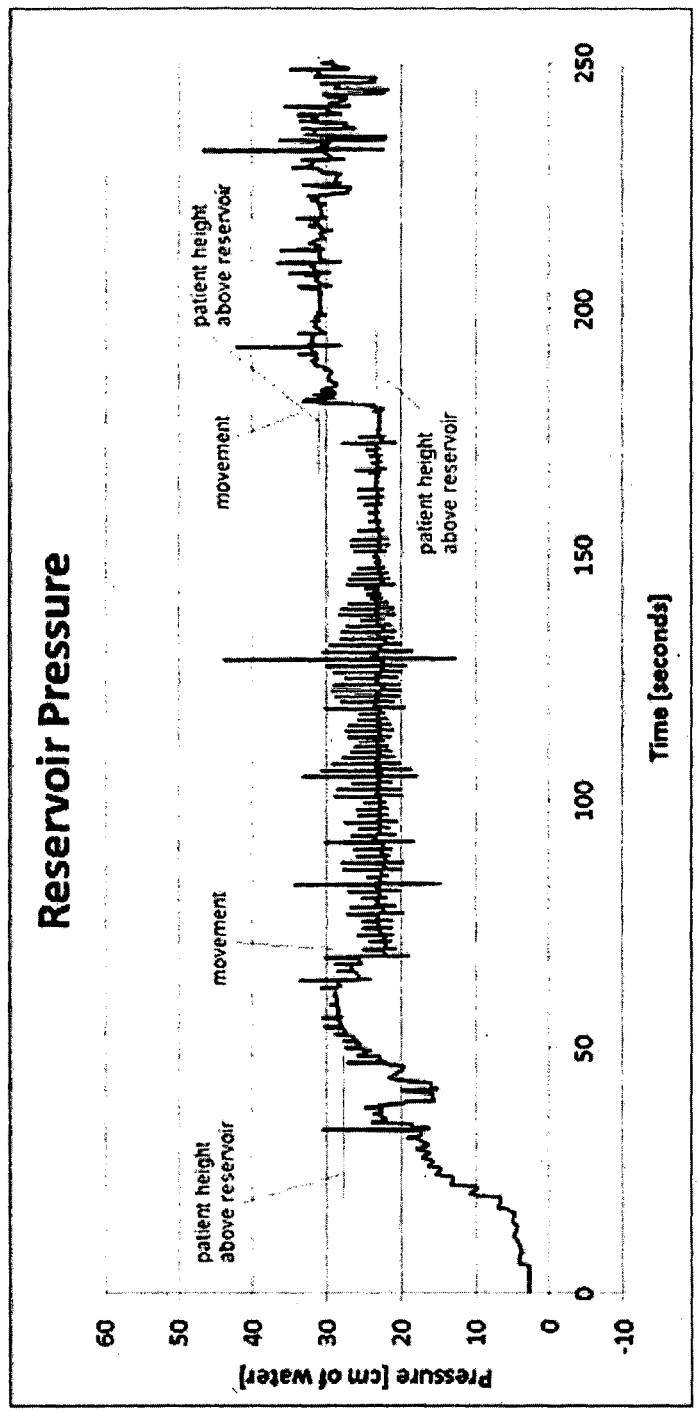

FIG. 22 is a chart illustrating reservoir pressure with respect to a methodology for controlling delivery of liquid humidification.

Figure 23:
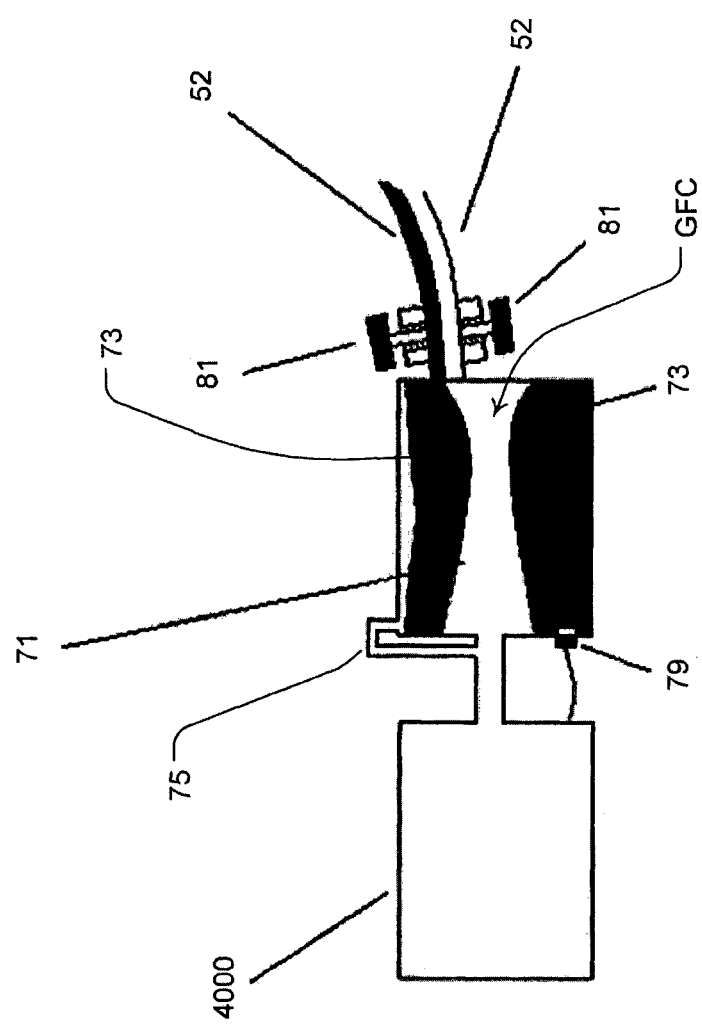

FIG. 23 is an illustration of a common water and gas control pump in some embodiments of the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share common characteristics and features. It is to be understood that one or more features of any one example may be combinable with one or more features of the other examples. In addition, any single feature or combination of features in any of the example or examples may constitute an additional feature which applicants may opt to independently protect.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. The respiratory therapy devices or blowers described herein may be designed to pump fluids other than air.

The term "Tidal Volume" will be taken herein to mean the volume of air transported into (or out of) the respiratory system during a single breath. The term "Minute Ventilation" will be taken herein to mean the volume of air transported into (or out of) the respiratory system in a minute and consequently:

Minute Ventilation=Tidal Volume×Breaths/Min.

Treatment Systems

Figure 1A:
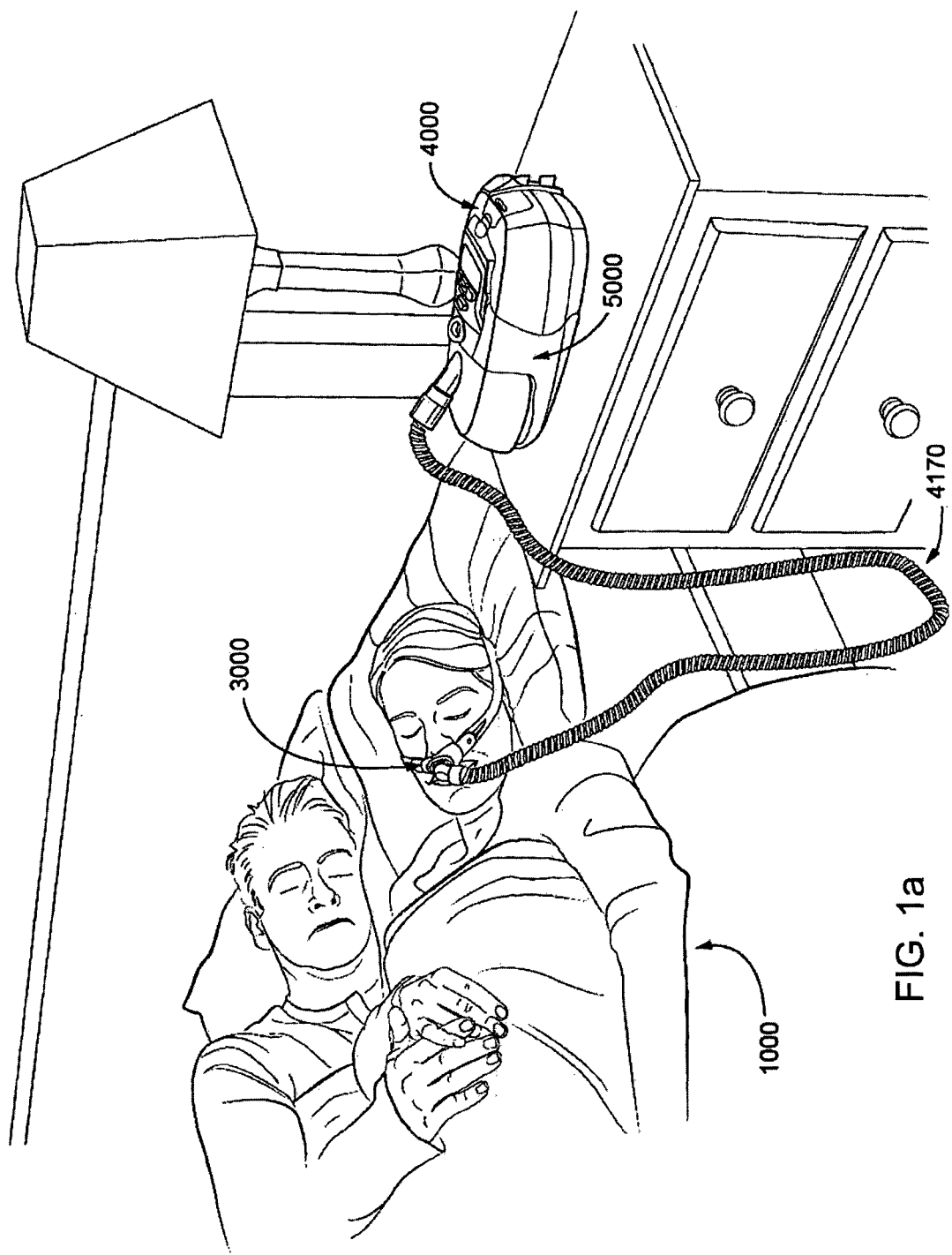
FIG. 1a shows a system relating to the present technology. A patient 1000 wearing a patient interface 3000, receives a supply of air at positive pressure from a PAP device 4000. Air from the PAP device is humidified in a humidifier 5000, and passes along an air circuit 4170 to the patient 1000.

In one form shown in FIG. 1a, the present technology comprises apparatus for treating a respiratory disorder. The apparatus may comprise a flow generator or blower for supplying pressurised respiratory gas (e.g., PAP device 4000), such as air, to the patient 1000 via an air delivery tube leading to a patient interface 3000.

Another form of a therapy system according to a certain embodiment of the present technology is shown in FIGS. 6a and 6b. The therapy system 100 includes a gas source 10 configured to provide a supply of pressurized breathable gas, such as a flow generator or a PAP device 4000 in FIG. 1a. Preferably the gas source 10 is coupled to a humidifier 20 configured to humidify the supply of pressurized gas. However in certain embodiments a humidifier may not be utilized. The gas source and optional humidifier may be coupled together via an air delivery conduit 30a. Alternatively, the humidifier may be integrated with the gas source 10 or adapted to directly couple to the gas source 20 as is known in the art. The gas source 10, when no humidifier is provided, or the humidifier 20 are coupled to a patient interface that is a sealed oral interface 50 via an air delivery conduit 30b. The sealed oral interface 50 is adapted to seal in or against the mouth of a patient 40 as discussed in more detail herein. As shown the patient 40 has an upper airway including a nasal cavity 44 and oral cavity 42 that interconnect and lead to the lower airways.

The gas source 10 may include a controller adapted to control the delivery of the pressurized gas to the oral interface 50. The gas source may include a positive airway pressure device or a ventilator, having a blower configured to pressurize a supply of air. The controller may be configured to control the speed of the blower to provide the desired supply of pressurized gas or the blower may be driven at a constant speed and the supply of pressurized gas controlled via a valve arrangement. Alternatively the gas source 10 may include a gas bottle or other such pressurized gas supply.

The gas source may also include one or more sensors to detect respiratory signals such as pressure or flow sensors and/or the gas source may include motor speed sensors such as Hall effect sensors that allow the estimating of the pressure or flow as described in co-pending U.S. Published Patent Application No. 2010/0319697, which is incorporated herein in its entirety.

Therapy

In use the therapy system 100 is configured to provide a supply of pressurized gas from the gas source 10 to a patient 40. As mentioned above the pressurized gas supply may be humidified by the humidifier 20 prior to delivery to the patient 40 via the oral interface 50. Whilst providing therapy the patient 50 may be breathing naturally via their nose such that fresh air enters and exits via the nasal cavity 44. The supply of pressurized gas is provided to the oral cavity 42 via the sealed oral interface 50 to assist in washing out or flushing out the carbon dioxide in the upper airway and effectively reducing the dead space of the nasal and oral cavities 42, 42. In this way the work of breathing is decreased for the patient.

Thus, in one form, the present technology comprises a method for treating a respiratory disorder by applying positive pressure to the entrance of the airways of a patient through an oral interface 50.

FIG. 7 provides an electro-pneumatic analogue model of such a therapy system indicating the path of the pressurized gas flow. The device or system 100 includes a gas source 10, such as a flow generator or blower, which generates a pressure supply $P_{FG}$. The pressure supply $P_{FG}$ is directed optionally via a humidifier (not shown in FIG. 7) through the air delivery tube 30 and into the oral cavity 42 of the patient 40 via an oral interface (not shown). The supply of gas delivered to the oral cavity 42 is then distributed to the nasal cavity 44 where it may exit to atmosphere 70 and/or travel to the lower airways 46. A further pressure source may be provided from the respiratory muscles 48, $P_{Mus}$ to assist in transporting the gas into and out of the respiratory system via contraction and expansion of the respiratory muscles. The different components in the air flow path provide different levels of impedance (Z) to the pressurized gas flows $P_{FG}$ and $P_{Mus}$. The air delivery tube 30 has an impedance, $Z_{tube}$, that reduces the pressure of the supply of gas that is delivered to the oral cavity 42. The oral cavity 42, nasal cavity 44 and lower airways 46 have impedances of $Z_{oral}$, $Z_{nasal}$ and $Z_{aw}$ respectively. The lower airways also have compliance of $C_{aw}$ due to the inflation and deflation of the lungs. These features can be used to characterize the system.

The pressurized gas may be controlled by the controller to be provided to the sealed oral interface 50 at a low constant level of flow, such as 1-20 Liters/minute (L/min), e.g., about 4 L/min, 5 L/min, 6 L/min, 7 L/min, 8 L/min, 9 L/min, 10 L/min, 11 L/min or 12 L/min. FIG. 8 shows a graph illustrating an example of providing a constant flow therapy at about 10 L/min over a single breath.

An estimate of the minute ventilation may be determined by the controller based on a measure of the nasal cavity and nasopharyngeal volume using a technique such as acoustic rhinometry or estimated based on patient characteristics such as height, weight, etc. Using the estimated minute ventilation the level of flow may be automatically adjusted to synchronize with the patient's breath. The therapy flow rate may be set to target displacement of the volume of air estimated to be contained in the patient nasal cavity before the start of inspiration.

Previous studies have shown that the average nasal cavity volume plus nasopharynx volume ranges between approximately 58 ml and approximately 81 ml.

In an alternative arrangement the pressurized gas may be provided to the sealed oral interface 50 at a low constant pressure level, such as 1-5 cmH$_2$O, e.g., about 2 cmH$_2$O, 3 cmH$_2$O or 4 cmH$_2$O. However, to prevent high oral pressures being generated due to blockages in the airways, for example, during a swallow, the impedance of the airway may be monitored by the controller and the pressure may be adjusted based on the determined airway impedance. For example, if a high airway impedance is determined then the controller may decrease the pressure or the control scheme of the controller may be automatically switched to a pressure control methodology which delivers a constant level of pressure (e.g., 2 cmH$_2$O).

The impedance of the patient airways may be determined based on an estimate of the pneumatic impedance between the outlet of the gas source ($P_{FG}$) and the atmosphere 70 (see FIG. 7). For example, the pneumatic impedance may be estimated based on the pressure measured at the outlet of the pressure source 10 divided by the flow through the therapy system 100.

Alternatively the pneumatic impedance can be calculated by monitoring the motor speed (angular velocity) and power (P=VI=I$^2$R). The power may be limited by limiting either the current or the voltage to reduce the pressure and the impedance. Furthermore, if the motor is driven with a pulse width modulation this may also be limited. In another arrangement, a blow off valve may be utilized if the impedance levels reach a predetermined or set level.

In another arrangement the pressure at the oral interface may be monitored by a pressure sensor. The pressure sensor may be located in or near the oral interface or near the pressure source and the pressure at the oral interface estimated based on previous characterization of the impedances of the air delivery tube and the oral interface. The pressure signal may be fed back in a control loop to ensure the pressure does not exceed a set pressure level.

In a further arrangement a flow sensor may monitor the level of flow in or near the oral interface. The flow signal may be fed back in a control loop to ensure the flow does not exceed a set flow level. However, this may not detect high oral pressure if the oral or nasal impedance becomes large, for example, during swallowing, however the control loop may be de-tuned to ignore large impedance changes that occur for only a short period of time.

The desired pressure may be set to a value that is a function of the patient's impedance, which would vary depending upon a patient's respiratory condition. A pressure limit may be determined as a function of the inverse of the impedance, such as proportional to the inverse of the impedance or another inverse relationship, for example:

$$P_{limit}(t) \propto \frac{1}{Z(t)},$$

or $$P_{limit}(t) \propto Z(t)^{-n}$$

Wherein n is a positive and real constant.

It might also be of benefit to have an offset in the relationship, such as $$P_{limit}(t) \propto \frac{1}{Z(t)} + c$$

The impedance may be monitored and recalculated repeatedly throughout therapy to monitor changes in impedance and prevent the occurrence of high pressures in the oral cavity. For example, the impedance may be recalculated with a sample rate of 5-50 Hz, such as 5 Hz, 10 Hz or 20 Hz.

The system may include a control system or controller having an algorithm(s) adapted to synchronize the delivery of the supply of pressurized gas to the oral interface with a patient's respiratory cycle. In the absence of therapy, estimates of the oral pressure waveform may be obtained from a pressure sensor located at or near the pressure source. Oral pressure fluctuates about the atmospheric baseline in accordance with the respiratory phase. The pressure may be expected to be negative on inspiration and positive on expiration. The pressure loss in conduits may be characterized as a function of flow, and may be determined and subtracted from the measured pressure at the pressure source to provide an estimate of the oral pressure. The high frequency oscillations not associated with breathing frequency, and artifacts introduced with swallowing, coughing, movements etc. may be filtered out, for example, with a low pass filter or moving average filter. Alternatively the pressure may be measured directly at or near the oral interface via a pressure sensor.

Flow therapy may then be controlled to deliver a volume of gas, for example via a sealed oral interface, at the end of expiration that matches the estimated volume of the nasal dead space. To achieve this timed delivery of flow, the expiratory endpoint should first be detected using the peak oral pressure, for example estimated from the pressure source as described above. As shown in FIG. 9 the flow delivery may be timed to trigger at a fixed percentage (x) of this peak value (P).

FIG. 10 shows a flow diagram indicating the steps of an algorithm configured to control the delivery of the supply of gas to the oral cavity based on detecting the pressure in the oral cavity. In step 600 the pressure is measured or estimated over time for a respiratory cycle to provide values for P(t). In step 602 the P(t) values are compared to detect the local peak in pressure (Pmax) during the respiratory cycle. Then in step 604 the pressure is continued to be monitored over time to detect when the pressure drops to a predetermined or set percentage (x %) of the peak value (Pmax). In step 606 once the predetermined or set percentage (x %) of the peak value has been reached the controller signals to the gas source to deliver a desired volume of air to the oral cavity. Such as with a Hamming window flow profile scaled to deliver the desired volume of gas.

FIG. 11 shows an example of controlling the delivery of the gas source to the oral cavity such that the gas supply is delivered in a smooth flow waveform, such as a half period of a cosine function, to improve patient comfort. The size of the smooth flow waveform may be scaled so that the integral is equal to the desired volume of gas to be delivered to wash out or flush out the oral and nasal cavity. FIG. 11 also shows an example of the oral therapy only being provided for a portion of the respiratory cycle, such as only at the end of expiration to assist in flushing out or washing out the oral and nasal cavities after each breath.

Alternatively, the oral therapy may be provided in additional portions (e.g., throughout) of the respiratory cycle, for example delivering the breathable gas to the oral cavity within inspiration and expiration. In such an example, during expiration, the addition of an oral (therapy) flow is introduced to the system so as to be directed towards the nasal dead space as a result of the expiratory air flow. As the tracheal flow decreases through the course of expiration, the ratio of breathable gas to the expired gas may increase. As a result, the patient's dead space may be filled with predominantly breathable gas rather than expired $CO_2$, allowing a higher concentration of breathable gas at the onset of inhalation than otherwise possible.

In some cases, it may be preferred to deliver the supply of breathable gas towards the posterior end of the mouth (towards the trachea). This may introduce the breathable gas further upstream of the flow during expiration, thereby increasing the effectiveness in washing or flushing out the dead space during expiration.

Oral therapy may be provided continuously throughout the respiratory cycle such that the low level of flow may provide some level of ventilator support to the patient during inspiration, for example by reducing the negative pressure or assisting with generating a positive end expiratory pressure (PEEP). The flow provided during the expiratory portion of the respiratory cycle would assist with washing or flushing out the dead space as discussed above.

The supply of pressurized gas from the gas source 10 may comprise air and/or oxygen. The oxygen may be combined with air to increase the concentration of oxygen over and above the typical concentration of oxygen present in air. In some cases, the oral therapy may only deliver oxygen.

The present technology may be used anytime; during the day or at night, awake or asleep to provide therapy assistance to a patient.

The present technology may be used to assist in exercise, such as for rehabilitation or sports training.

Humidification may be provided while providing oral therapy to prevent drying out of the airways, or the oral and/or nasal cavities. Humidity may be provided by any known humidification process including passover, heated passover, birdfeeder, bubble or diffuser, wicking, jet, pumped or counter flow humidification or any other such humidification system.

In certain arrangements where the therapy is provided to the mouth or oral cavity the humidification may be provided using liquid water supplied directly to the oral cavity. The liquid water may be pumped, birdfeed or otherwise supplied into the mouth via the oral interface at a predetermined or settable rate.

Patient Interface 3000

Mask Type Patient Interface 3000

A traditional mask-type non-invasive patient interface 3000 is illustrated in FIG. 3a. It will typically include the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to outwardly surround an entrance to the airways of the patient so as to facilitate the supply of air at positive pressure to the airways. In this way, an external seal is formed on the skin of the patient.

Oral Interface 50

Alternatively, FIG. 12 shows an example of an oral interface 50 that may be implemented to provide oral therapy. The oral interface 50 is adapted to fit within the mouth and provide a sealed arrangement in or against the mouth to prevent or limit air from leaking out of the mouth. The oral interface 50 includes a teeth engaging portion 54 and one or more gas delivery tubes 52 coupled therewith. The teeth engaging portion 54 may be configured to seal against the top teeth as shown. However, it is noted that the teeth engaging portion 54 may be configured to seal against the lower teeth or against both the upper and lower teeth. The one or more gas delivery tubes 52 provide gas supply into the oral cavity. As further illustrated in FIGS. 12 and 13, the teeth engaging portion may serve as a conduit for directing air supplied by the delivery tube 52 and through the teeth engaging portion toward the back and/or sides of the inside of the patient's mouth where the air is released. In some cases, such a device may provide the pressurized air treatment without an external skin contact seal surrounding the patient's mouth.

The oral interface device may be made of a soft pliable material that is adapted to seal against the teeth in use, such as silicone rubber, acrylic or other such pliable materials. Due to the use of low flows and/or low pressures during oral therapy the oral therapy device may be smaller and less intrusive and consequently provide less strain on the teeth and jaw compared to current oral interface devices.

In certain arrangements the oral interface device may also be designed to provide other benefits or to treat other disorders that the patient may have. For example the oral interface may be designed to prevent bruxism or jaw grinding by the patient. In other arrangements the oral interface may also be design to provide a mandibular advancement therapy to prevent or reduce the patient from having snoring, apnea and/or hypopnea events, in such cases the mandibular advancement device may be used to locate the oral flow therapy apparatus. The mandibular advancement device may be configured to a neutral position such that its primary purpose is to locate the oral flow therapy apparatus.

In certain arrangements the oral interface may be designed to provide a seal when the mouth is closed but to allow the patient to open their mouth and break the seal when desired, for example to allow the patient to talk. The oral interface may be designed such that the seal may be formed and broken repeatedly by closing and opening the mouth. In some cases a part of the seal may be formed by the patient's lips. In certain arrangements the system 100 may detect when the impedance drops below a first threshold and stop the therapy. The threshold may indicate that the oral interface is not sealed against the mouth. The device may also be able to detect when the impedance is above a second threshold, that indicates that the oral interface is sealed in or against the mouth, and commence therapy.

In a further alternative, a sealed nasal interface (not shown) may be provided to seal against or in one or more nares of a patient and the pressurized gas source is provide to the sealed nasal interface. If the sealed nasal interface seals against or in both nares a further device may be required to keep the patient's mouth open to allow the gas flow to wash out the nasal and oral cavities. For example the further device may include a straw-like device (not shown) that allows the air to flow out of the mouth via the straw-like device. Alternatively an obstructing device to prevent full closure of the mouth or other such device may be utilized. The supply of pressurized gas is preferably humidified prior to being provided to the nasal interface to prevent drying out of the airways or mouth.

Another version of an oral interface device for releasing air and/or water into the rear sides of the oral cavity are illustrated in FIGS. 14-19. The teeth engaging portion 54 of the device may be implemented to reside between the teeth and lips and/or between the teeth and a cheek surface within the mouth (i.e., inner cheek surface). The interface ends 53, which may typically reside between the teeth and inner cheek lining during use, may optionally be porous for the release of supplied gas and/or water. For example, an internal surface 53S of the ends (proximate to the teeth in use) may have a plurality of pores. Similarly, an external surface 53X of the ends (proximate to the inside of the cheek in use) may have a plurality of pores. The pores may be for gas supply and/or water permeation from the device. For example, some pores may be coupled with a conduit from a water supply/humidification device via one or more internal channels of the oral interface device and some pores may be coupled with a conduit of a gas source via one or more internal channels of the oral interface device. Still further, the oral interface device may have a release port 55, which may optionally be at each end 53, for gas and/or water supply depending on the pathways of the channel(s) of the teeth engaging portion 54 and the coupling of the supply conduit(s) (e.g., delivery tube 52). Generally, one or more conduit channels within the teeth engaging portion 54 will lead to the pores and release port from the supply conduit(s) 52.

In the oral interface device illustrated in FIGS. 14, 15 and 17 multiple delivery tubes 52 (e.g., dual conduits) are coupled or integrated with the oral interface device 50. Each of the conduits may be coupled either with a gas source or humidification/hydration source or both. For example, both may be coupled to a gas source. By way of further example, one may provide air and/or oxygen from a gas source and one may provide water. For example, as illustrated in FIG. 17, the channel(s) of one end 53 may lead to a delivery tube for delivery of hydration/humidification and the channels of the other end 53 may lead to a delivery tube for delivery of gas from a gas source.

However, in some cases, such as that illustrated in FIGS. 16 and 18, a single delivery conduit may be provided which may serve to deliver either gas or water, or, in some cases both. In the case of FIG. 16, the delivery conduit may have a single channel for either flow or gas delivery. In the example illustrated in FIG. 18, the delivery conduit 52 may be partitioned with multiple channels (e.g., bisected or trisected etc.) for discrete delivery of humidification/water and gas. As such, the ends 53 of the oral interface device may also be partitioned for discrete delivery. For example, in the device of FIG. 18, a single delivery conduit 52 has first and second channels 52CH1, 52CH2 that respectively lead to a set of pores at a top portion TP of the end 53 (above an end divider 57 which splits a cavity of the end 53) to provide a water delivery section and to a set of pores at the lower portion LP of the end 53 (below the end divider 57) to provide a gas delivery section. However, other partitioning schemes may be employed. For example, gas delivery may be made via the release ports 55 and/or the pores of the inner surface 53S while water delivery may be made via the pores of the outer surface 53X.

In the case of multiple delivery conduits, a splitter, y-connector or adaptor 59 as illustrated in FIG. 19 may be employed to implement a single supply conduit to the flow generator or PAP device. In some cases, such a single supply conduit from the flow generator and adapter may employ multiple channels to accommodate the discrete delivery of water and/or gas as necessary to the delivery conduits 52.

Accordingly, while the device may be used independent of other patient interfaces and for delivery of air, it may also be so implemented for the delivery of oxygen therapy. As such, it may be very efficient for delivering oxygen. By way of further example, the oral interface device as an oxygen delivery component may be combined with a nasal mask that provides a pressurized air therapy. Rather than increasing dead space, this would increase the volume to store oxygen. In this regard, the volume of the mask could be tuned (or otherwise chosen), and the oral flow rate of oxygen could be controlled or adjusted to maintain a sufficient oxygen flow rate to fill the nasal cavity and the mask. This can help to prevent (or control the amount of) rebreathing.

In some situations, the oral interface may implement a retaining clip 190 as shown in FIGS. 19A, 19B, 19C and 19D. The device may assist with positioning of one or more supply conduits with respect to the patient and may serve as an oral interface clip. In some cases, the clip 190 may be considered a cheek clip. The clip 190 may be placed partially within the patient's mouth so that first and second clip ends 191-1, 191-2 may ply against a user's or patient's cheek. In this regard, one of the clip ends would ply against an inside surface of the patient's cheek in the patient's mouth and the other end would ply against the outside of the patient's cheek. A clip arm 193 may extend between the clip ends and may provide an elastic or spring force to direct the clip ends toward each other and thereby help to maintain the clip ends in position on opposing sides of a cheek. Typically, the clip arm 193 will be integrated with one or more supply conduit(s) 195 and/or be coupled with a gas supply conduit to direct a flow of gas and/or liquid to the rear side of the user's mouth. One example of the supply conduit 195 is illustrated in FIG. 19A. In some cases as illustrated in the example of FIGS. 19B to 19C, the clip arm may include one or more conduit receiving slots 197 or other similar clip for attachment of one or more supply conduits. In some cases, a passage through the clip arm to an end of the clip arm may be implemented to direct a release of flow to the rear side of the user's mouth.

Either of the clip ends 191-1, 191-2 may optionally include a pad portion 194 for improved comfort and retention functionality. Such a pad portion may be constructed from a soft, compliant material to reduce incidence of high, localised forces. The pad portion may also be employed to increase the surface contact area with the cheek to help distribute the force.

In the examples of the figures, the curved spring structure (e.g., resilient pliable material or an elastic force material) of the clip arm is configured to resist movement once on the patient's cheek. Thus, the oral interface clip may be secured and retained on the patient by a clamping force. However, it should be understood that any number of other means of retention known in the art may be employed.

In general, the securement of the supply conduit to the oral interface clip, in conjunction with securement of the clip to the patient's cheek may allow for directing gas/liquid to a desired location within the patient's mouth (e.g., rear side) for extended periods of time. This may be advantageous as it may permit fewer adjustments and/or repositioning, leading to improved convenience and/or comfort.

It should be understood that the supply conduit, or a part thereof, may form a part of the retaining clip. For example, the retaining clip may be configured to include an outlet and/or a diffuser, and an inlet to receive a flow of breathable gases from a delivery conduit leading from a flow generator and/or a liquid from a liquid supply as described herein.

PAP Device 4000

A PAP device 4000 in accordance with one aspect of the present technology comprises mechanical and pneumatic components 4100, electrical components 4200 and is programmed to execute one or more algorithms. The PAP device has an external housing 4010 formed in two parts, an upper portion 4012 of the external housing 4010, and a lower portion 4014 of the external housing 4010. In alternative forms, the external housing 4010 may include one or more panel(s) 4015. The PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 comprises an inlet air filter 4112, an inlet muffler 4122, a controllable pressure device 4140 capable of supplying air at positive pressure (preferably a blower 4142), and an outlet muffler 4124. One or more pressure sensors 4272 and flow sensors 4274 are included in the pneumatic path.

The pneumatic block 4020 comprises a portion of the pneumatic path that is located within the external housing 4010.

The PAP device 4000 has an electrical power supply 4210, one or more input devices 4220, a central controller 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm modules, including in one implementation a pre-processing module, a therapy engine module, a pressure control module, and a fault condition module.

In what follows, the PAP device 4000 is referred to interchangeably as a ventilator.

PAP Device Mechanical & Pneumatic Components 4100

Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

Pressure Device 4140

In one form of the present technology, a pressure device 4140 for producing a flow of air at positive pressure is a controllable blower 4142. For example, the blower may include a brushless DC motor 4144 with one or more impellers housed in a volute. The blower is capable of delivering a supply of air, for example about 120 litres/minute, at a positive pressure in a range from about 4 $cmH_2O$ to about 20 $cmH_2O$, or in other forms up to about 30 $cmH_2O$.

In one form of the present technology the pressure and flow requirements of a pressure device 4140 may be greatly reduced compared with conventional PAP devices, such that it may only be required to deliver 4 to 25 litres/minute and 0 to 10 $cmH_2O$. This could enable the device to be scaled down in size, making it smaller and quieter than traditional pressure devices.

The pressure device 4140 is under the control of the therapy device controller 4240.

Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

Air Circuit 4170

An air circuit 4170 in accordance with an aspect of the present technology is constructed and arranged to allow a flow of air or breathable gasses between the pneumatic block 4020 and the patient interface 3000.

Oxygen Delivery 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000 or oral interface 54.

PAP Device Electrical Components 4200

Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

Central Controller 4230

In one form of the present technology, the central controller 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280 and humidifier controller 5250.

The processor 4230, or multiple such processors, may be configured to implement one or more methodologies described herein such as one or more algorithms expressed as computer programs stored in memory 4260. In some cases, as previously discussed, such processor(s) may be integrated with a PAP device 4000. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

Clock 4232

Preferably PAP device 4000 includes a clock 4232 that is connected to processor 4230.

Therapy Device Controller 4240

In one form of the present technology, therapy device controller 4240 is a pressure control module 4330 that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

Transducers 4270

Transducers may be internal of the device, or external of the PAP device. External transducers may be located for example on or form part of the air delivery circuit, e.g. the patient interface. External transducers may be in the form of non-contact sensors such as a Doppler radar movement sensor that transmit or transfer data to the PAP device.

Flow 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal or total flow Qt signal, from the flow transducer 4274, is received by the processor 4230. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor 4230. In one form, the signal from the pressure transducer 4272 is filtered prior to being received by the processor 4230.

Motor Speed 4276

In one form of the present technology a motor speed signal 4276 is generated. A motor speed signal 4276 is preferably provided by therapy device controller 4240. Motor speed may, for example, be generated by a speed sensor, such as a Hall effect sensor.

Data Communication Systems 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

Output Devices including Optional Display, Alarms 4290

An output device 4290 in accordance with the present technology may take the form of one or more of a visual, audio and haptic unit. A visual display may be a Liquid Crystal Display (LCD) or Light Emitting Diode (LED) display.

Display Driver 4292

A display driver 4292 receives as an input the characters, symbols, or images intended for display on the display 4294, and converts them to commands that cause the display 4294 to display those characters, symbols, or images.

Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

Therapy Device 4245

In a preferred form of the present technology, the therapy device 4245 is under the control of the control module 4330 to deliver therapy to a patient 1000 as discussed herein.

Preferably the therapy device 4245 is a positive air pressure device 4140 and/or a humidification therapy.

Humidifier 5000

In one form of the present technology there is provided a humidifier 5000 comprising a water reservoir and a heating plate 5240. Such a humidifier may provide water vapor in the air.

In another form of the present technology, the humidifier may be configured to provide a liquid humidification.

When delivering a breathable gas therapy to the airways of a therapy recipient, care typically needs to be taken to prevent discomfort and complications associated with drying of the airways. Traditional solutions generally involve a means of delivering humidification in the therapy gas. In such cases it may be of benefit to avoid delivering air-born water droplets (water in liquid form) because these can transport and deliver contaminants to the airways and cause further complications. For this reason, as well as for comfort, humidification in such systems is typically delivered in the form of humid air, where the moisture in the air has been vaporised. This greatly reduces the risk of transporting contaminants, such as bacteria, or particulates. Such a humidification system typically consists of a water reservoir, a heating component to heat the water, and a gas flow path in contact with the water in the reservoir, such that the gas mixes with the water vapour produced by the humidification system before being delivered to the patient. It is generally considered that condensation of the vapor in such a system is undesirable and uncomfortable. This is particularly the case when the therapy is delivered through the nasal passage, such as is often the case in CPAP, NIV, and HFT.

In some cases of the present technology, where in some embodiments the therapy gas may be delivered orally, via a sealed interface, it is desirable to avoid drying the oral or nasal passages, or other airways. This may be achieved in some embodiments by delivering humidification in a similar manor to the traditional humidification techniques associated with any therapy where the medium of delivery is a breathable gas. However, it may be preferable in an orally delivered therapy to deliver the humidification to the oral cavity in liquid form in such a way as to maintain the moisture levels that would naturally exist in a healthy individual due to salivary secretions in the oral cavity. An advantage of this aspect of the current invention is that it can utilise the body heat in the oral cavity to provide the heating for the humidification system. Liquid water is delivered to the oral cavity initially at ambient temperature. It may then take heat from the oral cavity, which in normal circumstances is maintained at around 37 degrees Celsius and thus provides a natural source of heat to vaporise the liquid in the oral cavity. Once in vapour form it can mix with the therapy gas and be delivered through the airways to the lungs (predominantly during inspiration), and to the nasal cavity (predominantly during expiration or cessation of patient respiratory flow).

In such cases, such a water delivery may be powered by gravity feed as illustrated in FIGS. 20 and 21. A gravity feed system will typically utilize a water reservoir, a patient interface, and a conduit connecting the reservoir to the patient interface. Optionally, the water flow rate may be controlled. For example, a hydrodynamic resistive element may be implemented between the reservoir and the patient. This may be achieved by, for example, a narrowing of the flow path of the conduit or by a resistance that is controllable/settable (e.g., a control valve). Such a humidification system may be configured as an oral humidification system (e.g., without other therapy as illustrated in FIG. 20), or may be implemented in conjunction with other therapies, such as the oral flow therapies described in more detail herein (e.g., as illustrated in FIG. 21).

The driving pressure may be approximated as the product of the water density, the gravitational acceleration and the vertical component of the distance between the top water level and the therapy delivery point as follows:

$P = \rho g h$ where:
- P=driving pressure;
- ρ=water density;
- g=gravitational acceleration; and
- h=vertical distance from the top water level to the delivery point.

In an alternative embodiment the reservoir may be filled with a liquid source of nourishment (e.g., mango lassi) or other fluid containing medication, as a means of drug delivery.

In an alternative embodiment, the water delivery may be powered by a water pump. In this case, it may allow the water delivery to act against gravitational forces. For example, the water reservoir may be fitted with a pressure sensor, or other sensor from which the water pressure may be derived. In such an embodiment the system may be set up for use with the water delivery tube being full of water when coupled with a patient interface engaged with the patient. A controller may then determine from the pressure sensor (or pressure derived from other sensor(s)) the pressure created by the gravitation acceleration on the water column. If pressure is measured in units of centimetres of water the pressure and the water delivery tube is full of water, the pressure reading may be taken to represent the height of the patient interface above the sensor in the reservoir. The graph of FIG. 22 illustrates an example of such a pressure signal. The pressure may initially match the height of the water in the reservoir. A controller may control the pump in accordance with the measured pressure so as to engage it to gradually increase the measured pressure at the sensor until a calculated average of the pressure plateaus. Such a plateau pressure may be taken to correspond to the height of the patient interface above the pressure sensor. The pump can then be further engaged to deliver liquid to the patient against the determined gravitational load. If the measured pressure is averaged over a number of samples, and the average pressure changes by a predetermined (or user defined) threshold amount, this could be taken as an indication of patient movement. In the event of such a detection and after the averaged pressure has stabilized to within some threshold of values, a new patient interface height can be established (by the previously described plateau detection process). Thereafter, the pump can be engaged to deliver liquid against the new gravitational load. If the pressure appears to drop at an approximately constant rate, this could indicate syphoning, and the pump may be disengaged.

In an alternative embodiment, the gas and liquid may be powered by the same pump. In such a case it may be preferable to limit the flow of gas with a collapsible tube 71 such as that illustrated in FIG. 23 serving as a gas flow channel GFC and a flow reservoir 73. A fluid pressure sensor 79 may be provided to permit the controller of the flow generator to determine the fluid pressure. The tube 71 may be tuned with the appropriate dimensions and stiffness to provide tube flow limitation at the desired therapy flow, for example, about 5, 10, 15, 20, or 25 litres per minute. Tube flow limitation is characterised by the phenomenon that an increase in back pressure does not produce an increase in flow. This phenomenon has been well studied in collapsible tubes. As such, the back pressure supplied by pressure line 75 may be implemented to control the liquid delivery rate independent of the gas flow rate. In some embodiments, it may be desirable to have a high resistance coupling (not shown) between the gas flow generator or PAP 4000 and the water reservoir 73 to slowly equalise the pressure between the two systems as the water level reduces during therapy.

In some such cases, it may be preferable to put controllable resistive loads 81 on both the liquid and gas delivery systems, which may be electro-mechanical when controlled by the controller of the flow generator. It may be desirable to have these at either the flow generator end of the circuit or closer to the patient end of the circuit for ease of patient control of therapy or comfort, or somewhere in between the two.

In some cases, the fluid delivery to the patient interface may be controlled by the controller to be activated at certain times and/or to provide certain quantities. For example, in some cases, a button on the respiratory treatment apparatus may be configured to trigger a short delivery of fluid (e.g., a small amount) on demand. For example, the user might press the button which activates delivery of a small quantity of fluid. In some cases, fluid may be automatically delivered at certain times that are detected or scheduled by the controller. For example, the controller may be configured (e.g., to activate a pump or open a controlled valve) to deliver some fluid based on a detection of the patient respiratory cycle. For example, the controller may be configured to determine a suitable time and/or quantity of fluid to deliver based on a count of respiratory cycles. Such a configuration may take into account the quantity of water that would evaporate based on a number of detected respiratory cycles or time of use and replenish the water accordingly. In some cases, fluid may be delivered at the time of detected patient expiration or an expiratory pause so as to avoid delivery of fluid during patient inspiration. In some cases, the controller may be configured to prevent a delivery of fluid during detected patient inspiration. Other suitable times and quantities may also be implemented.

In some cases a target mass of fluid to be delivered may be calculated. The target mass delivery rate may be based on an estimate of evaporation of fluid inside the mouth.

One example of deriving the suitable quantity of fluid delivery would be by use of the relationship $m = c \times V$, where m=mass of fluid (inside the mouth), c=proportionality constant, and V=volume of air (inside the mouth). A derivative of this equation with respect to time may be taken to find the mass rate of evaporation inside the mouth, or target mass rate of delivery of fluid to maintain equilibrium based on the volume flow rate of gas delivered. The proportionality constant may be estimated as a function of the therapy gas temperature and oral surface temperature, assumed to be in the order of 37 degrees Celsius. Optionally, such temperatures may be measured by the controller if one or more temperature sensors are implemented (e.g., a thermistor in a gas flow path of the flow generator and/or a thermistor of the oral interface.) Alternatively a look-up table may be used (e.g., stored in memory and accessed by the processor/controller) correlating the proportionality constant to the measured therapy gas temperature and/or the oral surface temperature. Alternatively an approximate value may be based on average conditions for example 29.2 $g/m^3$ published by Sha Li Et al. In some cases, the controller may integrate the gas flow signal from the flow sensor (e.g., sum the digital samples of a flow signal attributable to the supplied gas) and multiply that value by the proportionality constant the gives the target fluid mass rate to deliver. The controller may then control the fluid delivery rate in accordance with the calculated target fluid mass rate. In some cases the target may be increased or decreased above or below the calculated value for comfort, for example according to patient preference. In some such cases, the increase or decrease value may be a setting of the controller adjustable by a user via a user interface of the apparatus.

Advantages of Some Features of the Technology

Washing out or flushing out the oral and/or nasal cavities with a supply of breathable gas assists in reducing minute ventilation and consequently the patient or user's work of breathing. Reducing the work of breathing assists in alleviating many of the problems associated with a number of respiratory disorders.

Types of respiratory disorders that may be treated using oral therapy may include lung diseases such as emphysema, Chronic Obstructive Pulmonary Disease (COPD), Pulmonary Embolism, Pulmonary Vasulitis, Acute Respiratory Distress Syndrome (ARDS), Pulmonary Fibrosis or other such respiratory disorders.

Some examples of the present technology may reduce the pressures needed for therapy such that smaller oral interfaces may be utilized that are more comfortable and less intrusive.

Such devices may provide improved comfort to the patient and in certain embodiments may allow the patient to talk.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the technology. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the technology may have particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

Glossary

For purposes of the present technology disclosure, in certain forms of the present technology, one or more of the following definitions may apply. In other forms of the present technology, alternative definitions may apply.

General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

APAP: Automatic Positive Airway Pressure. Positive airway pressure that is continually adjustable between minimum and maximum limits, depending on the presence or absence of indications of SDB events.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Motor: A device for converting electrical energy into rotary movement of a member. In the present context the rotating member is an impeller, which rotates in place around a fixed axis so as to impart a pressure increase to air moving along the axis of rotation.

Positive Airway Pressure (PAP) device: A device for providing a supply of air at positive pressure to the airways.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

Volute: The casing of the centrifugal pump that receives the air being pumped by the impeller, slowing down the flow rate of air and increasing the pressure. The cross-section of the volute increases in area towards the discharge port.

Aspects of the Respiratory Cycle

Apnea: An apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
  (i) Flattened: Having a rise followed by a relatively flat portion, followed by a fall.
  (ii) Chair-shaped: Having a single local peak, the peak being at the leading edge, followed by a relatively flat portion.
  (iii) Reverse-chair shaped: Having a relatively flat portion followed by single local peak, the peak being at the trailing edge.
  (iv) M-shaped: Having two local peaks, one at the leading edge, and one at the trailing edge, and a relatively flat portion or a dip between the two peaks.

Hypopnea: A hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the PAP device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow. When expressed as a volume per minute, this quantity is often referred to as "minute ventilation". Minute ventilation is sometimes given simply as a volume, understood to be the volume per minute.

PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: A flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. For nasal CPAP treatment of OSA, a reference to treatment pressure is a reference to a pressure in the range of about 4-20 $cmH_2O$, or about 4-30 $cmH_2O$. The pressure in the patient interface (or, more succinctly, mask pressure) is given the symbol Pm.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound power is usually given in decibels SPL, that is, decibels relative to a reference power, normally taken as $20 \times 10^{-6}$ pascal (Pa), considered the threshold of human hearing.

Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: a parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP (or EEP): a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the device aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

Ventilator inspiration and ventilator expiration: the periods during which the ventilator considers that it should deliver pressures appropriate respectively to patient inspiration and expiration. Depending on the quality of patient-ventilator synchronisation, and the presence of upper airway obstruction, these may or may not correspond to actual patient inspiration or expiration.

Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

Additional Technology Examples

A respiratory apparatus fitted to deliver an oral therapy comprising:
 a supply conduit,
 a mouth piece including a teeth engaging portion coupled with the supply conduit, the teeth engaging portion configured as a channel to conduct a flow of the supply conduit, the teeth engaging portion comprising first and second end release ports;
 whereby a flow of gas or water may be provided to a rear side of the oral cavity of a patient with the first or second end release ports.

The respiratory apparatus of the preceding paragraph wherein the teeth engaging portion comprises first and second sets of pores.

The respiratory apparatus of the preceding paragraph wherein the first and second sets of pores are on first and second ends of the teeth engaging portion.

The respiratory apparatus of any of the preceding paragraphs wherein the first set of pores is configured to deliver a gas therapy.

The respiratory apparatus of any of the preceding paragraphs wherein the second set of pores is configured to deliver a humidification therapy.

The respiratory apparatus of the preceding paragraph wherein the humidification therapy comprises a liquid.

The respiratory apparatus of any of the preceding paragraph wherein the liquid is water.

The respiratory apparatus of any of the preceding paragraphs further comprising a gas flow generator.

The respiratory apparatus of any of the preceding paragraphs further comprising a liquid flow generator.

The respiratory apparatus of the preceding paragraph wherein the liquid flow generator comprises any of (a) a reservoir and a gravity feed coupling the reservoir with a channel of the supply conduit; (b) a reservoir and pump; or (c) a flow generator and a reservoir with a collapsible tube.

The respiratory apparatus of the any of the preceding paragraphs comprising a controller, the controller including at least one processor, the controller configured to control a delivered gas.

The respiratory apparatus of the preceding paragraph wherein the controller is configured to control a gas delivered by the mouth piece in accordance with a determined impedance.

The respiratory apparatus of the preceding paragraph wherein the controller is configured to decrease a pressure of the controlled gas delivered by the mouth piece in accordance with a detection of an impedance indicative of an airway blockage.

The respiratory apparatus of any of the preceding paragraphs comprising a controller, the controller including at least one processor, the controller configured to control a delivered gas as a function of detected peak pressure.

The respiratory apparatus of any of the preceding paragraphs comprising a controller, the controller including at least one processor, the controller configured to control a delivered liquid.

The respiratory apparatus of the preceding paragraph wherein the controller is configured to control the delivered liquid in accordance with a determined water pressure.

The respiratory apparatus of the preceding paragraph wherein the controller is configured to control delivery of the liquid subsequent to a detection of an average pressure plateau.

The respiratory apparatus of any of the preceding paragraphs wherein the supply of pressurized breathable gas comprises air and/or oxygen.

The respiratory apparatus of the preceding paragraph, wherein a controller is further configured to control a concentration of oxygen in the supply of pressurized breathable gas.

The respiratory apparatus of any of the preceding paragraphs, wherein a controller is further configured to control a flow rate of oxygen in the supply of pressurized breathable gas.

A respiratory apparatus for providing therapy to a patient to reduce a work of breathing and stabilise blood gasses comprising an oral interface adapted to provide sealed communication to the patient's oral cavity and direct a release of flow of gas to a rear side of the oral cavity.

The respiratory apparatus of the preceding paragraph further comprising a breathable gas source with an enriched oxygen level to provide a supply of pressurized breathable gas to the oral interface.

The respiratory apparatus of the preceding paragraph further comprising a controller configured to control the delivery of the supply of pressurized oxygen enriched breathable gas to the oral interface during at least a portion of the patient's respiratory cycle.

The respiratory apparatus of the preceding paragraph wherein the oxygen concentration and the flow rate may be controlled independently to stabilise blood gasses and reduce a work of breathing respectively.

A respiratory apparatus for providing a therapy to a patient comprising an oral interface adapted to provide sealed communication to the patient's oral cavity and direct a release of flow of gas to a rear side of the oral cavity.

The respiratory apparatus of any of the preceding paragraphs wherein the oral interface comprises (a) a mouth piece including a teeth engaging portion coupled with the supply conduit, the teeth engaging portion configured as a channel to conduct a flow of the supply conduit, the teeth engaging portion comprising first and second end release ports; and/or (b) a cheek engaging portion coupled with the supply conduit, the cheek engaging portion comprising a cheek clip.

The respiratory apparatus of the preceding paragraph wherein the cheek clip comprises first and second clip ends.

The respiratory apparatus of the preceding paragraph wherein either of the first and second clip ends comprises a pad.

The respiratory apparatus of the preceding paragraph wherein the cheek clip further comprises a supply conduit receiving slot.

A respiratory apparatus for providing a therapy to a patient comprising an oral interface adapted to provide sealed communication to the patient's oral cavity and direct a release of flow of liquid to a rear side of the oral cavity.

The respiratory apparatus of the preceding paragraph further comprising a controller to control the release of the flow of liquid.

The respiratory apparatus of any of the preceding paragraphs wherein the controller is configured to control the release of flow based on a detection of a respiratory cycle.

The respiratory apparatus of the preceding paragraph wherein the controller is configured to determine a quantity of liquid to release.

The respiratory apparatus of the preceding paragraph wherein the controller calculates a flow rate quantity based on an evaporation estimate.

The invention claimed is:

1. An apparatus for providing therapy to a patient to reduce a work of breathing, the apparatus comprising:
   an oral interface configured for insertion into the patient's oral cavity to direct a release of a flow of gas to a rear side of the oral cavity;
   a breathable gas source to deliver a supply of pressurized breathable gas to the oral interface; and
   a controller configured to monitor the patient's impedance comprising oral cavity impedance and nasal cavity impedance, and control, in accordance with the oral cavity impedance and/or the nasal cavity impedance, the delivery of the supply of pressurized breathable gas to the oral interface during at least a portion of the patient's expiratory phase of a respiratory cycle to wash out carbon dioxide from the patient's oral and/or nasal cavities.

2. The apparatus of claim 1, further comprising a humidifier to humidify the pressurized breathable gas.

3. The apparatus of claim 2, wherein the humidifier is configured to provide a supply of liquid water to the oral interface.

4. The apparatus of claim 1, wherein the controller is further configured to synchronize the delivery of the supply of pressurized breathable gas to be delivered at an end portion of the patient's expiration phase to wash out carbon dioxide from the patient's oral and/or nasal cavities.

5. The apparatus of claim 1, wherein the supply of pressurized breathable gas is delivered continuously throughout the respiratory cycle.

6. The apparatus of claim 1 wherein the controller is further configured to control a flow rate or concentration of oxygen in the supply of pressurized breathable gas.

7. The apparatus of claim 1 wherein the controller is configured to decrease a pressure of the supply of pressurized breathable gas in accordance with a detection of an impedance indicative of an airway blockage.

8. The apparatus of claim 1 wherein the oral interface comprises first and second release ports configured for gas release at opposing sides of the patient's oral cavity.

9. The apparatus of claim 8 wherein the first and second release ports are configured to reside between the teeth and inner cheek lining during use.

10. The apparatus of claim 1, wherein the oral interface includes a teeth engaging portion, the teeth engaging portion adapted to direct the flow of gas to the rear side of the oral cavity to wash out carbon dioxide from the patient's oral and/or nasal cavities.

11. The apparatus of claim 10 wherein the teeth engaging portion is configured to reside between teeth and lips and/or between teeth and a cheek surface within the oral cavity.

12. The apparatus of claim 10 wherein the teeth engaging portion is configured as a seal to permit washout of carbon dioxide from the oral cavity through a nasal cavity.

13. The apparatus of claim 1 wherein a seal of the oral interface is configured to permit washout of carbon dioxide from the oral cavity through a nasal cavity.

14. An apparatus for providing therapy to a patient to reduce a work of breathing, the apparatus comprising:
   an oral interface adapted to provide sealed communication to the patient's oral cavity and direct a release of a flow of gas to a rear side of the oral cavity;
   a breathable gas source to deliver a supply of pressurized breathable gas to the oral interface; and
   a controller configured to monitor the patient's impedance comprising oral cavity impedance and nasal cavity impedance, and control, in accordance with the oral cavity impedance and/or the nasal cavity impedance, the delivery of the supply of pressurized breathable gas to the oral interface during at least a portion of the patient's expiratory phase of a respiratory cycle to wash out carbon dioxide from the patient's oral and/or nasal cavities.

* * * * *